(12) United States Patent
Zhang et al.

(10) Patent No.: US 9,315,496 B2
(45) Date of Patent: Apr. 19, 2016

(54) BENZOPYRONE DERIVATIVE AND USE THEREOF

(75) Inventors: Guisen Zhang, Xuzhou (CN); Yin Chen, Xuzhou (CN); Xiangqing Xu, Xuzhou (CN); Bifeng Liu, Wuhan (CN); Xin Liu, Wuhan (CN); Song Zhao, Xuzhou (CN); Shicheng Liu, Xuzhou (CN); Minquan Yu, Xuzhou (CN); Heng Zhang, Wuhan (CN); Xinghua Liu, Xuzhou (CN)

(73) Assignees: HUAZHONG UNIVERSITY OF SCIENCE & TECHNOLOGY, Wuhan (CN); NHWA PHARMA CORPORATION, Xuzhou (CN)

( * ) Notice: Subject to any disclaimer, the term of this patent is extended or adjusted under 35 U.S.C. 154(b) by 258 days.

(21) Appl. No.: 14/009,581

(22) PCT Filed: Apr. 6, 2012

(86) PCT No.: PCT/CN2012/073588
§ 371 (c)(1),
(2), (4) Date: Dec. 17, 2013

(87) PCT Pub. No.: WO2012/136147
PCT Pub. Date: Oct. 11, 2012

(65) Prior Publication Data
US 2014/0113911 A1    Apr. 24, 2014

(30) Foreign Application Priority Data

Apr. 7, 2011    (CN) .......................... 2011 1 0086701

(51) Int. Cl.
| | | |
|---|---|---|
| *A61K 31/496* | (2006.01) | |
| *A61K 31/454* | (2006.01) | |
| *C07D 405/12* | (2006.01) | |
| *C07D 405/14* | (2006.01) | |
| *C07D 413/12* | (2006.01) | |
| *C07D 413/14* | (2006.01) | |
| *C07D 417/12* | (2006.01) | |
| *C07D 417/14* | (2006.01) | |

(52) U.S. Cl.
CPC ............ *C07D 417/12* (2013.01); *A61K 31/454* (2013.01); *A61K 31/496* (2013.01); *C07D 405/12* (2013.01); *C07D 405/14* (2013.01); *C07D 413/12* (2013.01); *C07D 413/14* (2013.01); *C07D 417/14* (2013.01)

(58) Field of Classification Search
None
See application file for complete search history.

(56) References Cited

U.S. PATENT DOCUMENTS 9,018,213 B2 *   4/2015   Zhang ................. C07D 413/14
                                                      514/254.04

FOREIGN PATENT DOCUMENTS

| CN | 85106970 A | 4/1987 |
|---|---|---|
| CN | 101258147 A | 9/2008 |
| CN | 102206214 | * 11/2011 |
| CN | 102267971 A | 12/2011 |
| WO | WO 99/35144 | 7/1999 |

OTHER PUBLICATIONS

Yagcioglu, Turkish Journal of Psychiatry, vol. 18(4), p. 1-10 (2007).*
Gonzlex-Gomez J. C. et al. "New Arylpiperazine Derivatives with High Affinity for $\alpha_{1A}$, $D_2$ and 5-$HT_{2A}$ Receptors" Blooraanic & Medicinal Chemistry Letters 13 (2003) 175-178 Science Direct.

* cited by examiner

*Primary Examiner* — Emily Bernhardt
(74) *Attorney, Agent, or Firm* — Mark S. Cohen; Pearl Cohen Zedek Latzer Baratz LLP

(57) ABSTRACT

The present invention relates to the field of pharmaceutical chemistry, and in particular, to a benzopyrone derivative and a use thereof. The benzopyrone derivative is compound having a structure of formula (I) or a pharmaceutically acceptable salt thereof. It has been found by experiments that, this type of compounds is useful in prevention or treatment of neuropsychical diseases.

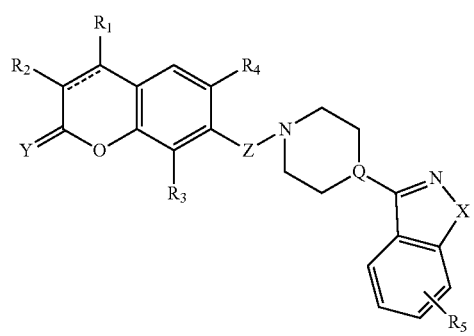

13 Claims, No Drawings

BENZOPYRONE DERIVATIVE AND USE THEREOF

CROSS-REFERENCE TO RELATED APPLICATION

This application is a National Phase Application of PCT International Application No. PCT/CN2012/073588, International Filing Date Apr. 6, 2012, claiming priority of Chinese Patent Applications, 201110086701.8, filed Apr. 7, 2011, all of which are incorporated herein by reference in their entirety.

TECHNICAL FIELD

The invention relates to the medicinal chemistry field. In particular, the invention relates to a benzopyrone derivative and the use thereof for the treatment of psychoneurosis.

BACKGROUND

Schizophrenia is a type of disease characterized in severely schizophrenic cognition and emotion, presenting as the influence on the basic behavior of a human, such as language, thinking, feeling, self-perception or the like. This disease encompasses a large variety of disorders, such as those involved in psyche, e.g. delusion, paranoia, illusion or the like.

Schizophrenia is the most serious mental disease. About 1% of the people all over the world suffer from schizophrenia, and only 5% of them can be cured after treatments. In addition, schizophrenia is always accompanied with various complications, e.g. anxiety, depression, psychic drug abuse or the like. It was shown in a study by Datamonitor that over ⅓ of the patients with schizophrenia suffer from one or more complicated psychoses or cognitive disorders.

The anti-psychosis drug exerting its pharmacological action by blocking dopamine $D_2$ receptor is conventionally known as the $1^{st}$ generation anti-psychosis drug, i.e. the "typical" anti-psychosis drug (e.g. haloperidol). This drug is effective for schizophrenia positive symptoms, but not effective for negative symptoms and cognitive disorders. Furthermore, the typical anti-psychosis drug generally has serious EPS side effects and is not effective for ⅓ of the patients with schizophrenia.

A series of new anti-psychosis drugs have been developed since 1960s, including ziprasidone, risperidone or the like, which are considered as the $2^{nd}$ generation anti-psychosis drug (the novel anti-psychosis drug). Although these drugs have different pharmacological actions, they share the same pharmacological properties, i.e. the affinities for $5\text{-}HT_{2A}$ receptor and noradrenalin (NA) receptor ($\alpha 1$, $\alpha 2$) are much higher than those for $D_2$ receptor, resulting the decrease of the ratio $D_2/5\text{-}HT_{2A}$. Their clinical effects are more advantageous over those of the $1^{st}$ generation anti-psychosis drugs, since they are effective for the positive symptoms like the conventional anti-psychosis drug, and are effective for the negative symptoms and cognitive defect symptoms and have broader application spectrum. However, these drugs have the side effects of extended QT interval, hyperprolactinemia, weight gain or the like. Therefore, it is needed to find a new drug, which is effective for schizophrenia positive and negative symptoms and cognitive disorders, and has fewer side effect.

Aripiprazole belongs to a butyl benzene prazosin compound, which was approved by FDA in November, 2002. This drug has a particular action mechanism as having high affinities with dopamine $D_2$, $D_3$, $5\text{-}HT_{1A}$ and $5\text{-}HT_{2A}$ receptors, and medium affinities with $D_4$, $5\text{-}HT_{2C}$, $5\text{-}HT_7$, $\alpha 1$, H1 receptors and 5-HT essential absorbing site. Aripiprazole exerts its effect against schizophrenia through its partial agonistic action for $D_2$ and $5\text{-}HT_{1A}$ receptors and antagonistic action for $5\text{-}HT_{2A}$ receptor, and has the effect of stabilizing dopamine systemic activity. Clinical trials have shown that aripiprazole is effective for both the positive and negative symptoms of schizophrenia, and its long-term application can reduce the reoccurrence of schizophrenia, and improve emotion and cognitive function disorders. Moreover, its EPS side effects and the effect of increasing serum prolactin level are less than those of the conventional anti-psychosis drug or the above non-typical anti-psychosis drug.

5-hydroxy tryptamine system plays an important role in modulating the function of prefrontal cortex (PFC), including emotion control, cognitive behavior and working memory. The pyramidal neurons and GABA interneurons of PFC contain several 5-hydroxy tryptamine receptor subtypes $5\text{-}HT_{1A}$ and $5\text{-}HT_{2A}$ in high density. It has been shown recently that PFC and NMDA receptor channels are the targets of $5\text{-}HT_{1A}$ receptor, and these two receptors modulate the excitatory neuron of cerebral cortex, thereby affecting the cognitive function. In fact, various preclinical data have shown that $5\text{-}HT_{1A}$ receptor may be the new target of the development of anti-psychosis drug. The high affinity of non-typical anti-psychosis drug (e.g. olanzapine, aripiprazole or the like) to $5\text{-}HT_{1A}$ receptor and its low EPS side effects indicate that 5-hydroxy tryptamine system plays an important role in modulating the function of prefrontal cortex (PFC), including emotion control, cognitive behavior and working memory. It has been shown recently that $5\text{-}HT_{1A}$ agonist is associated with non-typical anti-psychosis drug therapy, which can improve negative symptoms and cognitive disorders. In the treatment of schizophrenia with the non-typical anti-psychosis drug clozapine, it was found that $5\text{-}HT_{2A}$ plays an important role in various aspects, including cognition, emotion regulation and motion control. The blocking of $5\text{-}HT_{2A}$ receptor can normalize the release of dopamine, exerting the effect of anti-psychosis. In addition, $5\text{-}HT_{2C}$ receptor is closely related with weight gain.

The distribution of $D_3$ receptor in brain mainly locates specifically at limbic system and there are two major DA neural pathways in brain: one is nigrostriatal pathway regulating the motion function, while the other is mesencephalic ventral tegmental area-accumbens nucleus-prefrontal cortex. DA pathway is closely associated with learning cognition and emotion behavior, of which the disorder will lead to schizophrenia. This DA pathway is the main pathway of reward effect in brain. $D_3$ receptor is distributed in both of the DA neural pathways, and has complex interaction with other DA receptor subtypes, and thus may be the target of anti-psychosis drug therapy. Selective $D_3$ receptor antagonism can reduce the negative and cognitive symptoms of schizophrenia, which can additionally prevent extrapyramidal system side effects, including tardive dyskinesia, Parkinson's disease or the like. Therefore, it is needed to find novel anti-schizophrenia drug which can bind to multiple receptors and has less side effects clinically.

SUMMARY

It is the object of the invention to provide a novel benzopyrone derivative with activity based on the prior art.

It is another object of the invention to provide a method for treating neuropsychical disease, comprising administrating the benzopyrone derivative according to the invention to the patient in need thereof.

It is another object of the invention to provide the use of the above-mentioned benzopyrone derivative in the manufacture of a medicament for the treatment or prevention of neuropsychical disease.

The objects of the invention can be achieved by the following solutions.

A benzopyrone derivative having the structure of formula (I) or a pharmaceutically acceptable salt thereof,

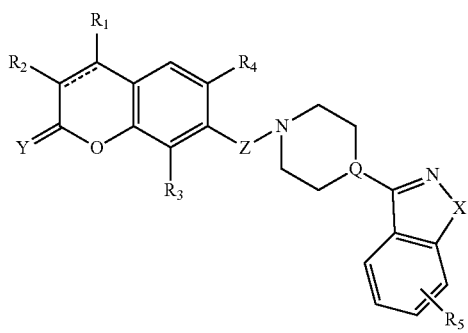

wherein,

Z is —(CH$_2$)$_n$, which is unsubstituted or substituted by one or more substituents independently selected from the group consisting of hydroxyl and C$_{1-5}$alkyl, wherein n is an integer of 2-6, and the carbon chain of Z optionally has a double bond(s)

Y is O or S;

Q is N or CH;

X is O, S or NH;

the dashed line represents a single bond or a double bond;

R$_1$, R$_3$, R$_4$ and R$_5$ are each independently H; halogen; cyano; hydroxyl; C$_{5-14}$aryl, which is unsubstituted or substituted by one or more substituents independently selected from the group consisting of halogen, amino and hydroxyl; C$_{1-5}$alkyl, which is unsubstituted or substituted by one or more substituents independently selected from the group consisting of halogen, amino and hydroxyl; or C$_{1-5}$alkoxy, which is unsubstituted or substituted by one or more substituents independently selected from the group consisting of halogen, amino and hydroxyl; wherein the halogen is preferably Cl or F;

R$_2$ is H; or C$_{1-5}$alkyl, which is unsubstituted or substituted by one or more substituents independently selected from the group consisting of halogen, amino and hydroxyl.

Preferably, in formula (I), Z is —(CH$_2$)$_n$, which is unsubstituted or substituted by one or more hydroxyl, n is an integer of 2-5, and the carbon chain of Z optionally has a double bond(s); and most preferably, n is 3, 4 or 5.

Preferably, in formula (I), Y is O; X is O or S.

Preferably, in formula (I), R$_1$ is H, phenyl, halophenyl, C$_{1-5}$alkyl, C$_{1-5}$haloalkyl or C$_{1-5}$hydroxylalkyl, wherein the halogen (halo) is preferably Cl or F. Most preferably, R$_1$ is H, phenyl, methyl, ethyl, propyl, trifluoromethyl or hydroxymethyl.

Preferably, in formula (I), R$_3$, R$_4$ and R$_5$ are each independently H, halogen or C$_{1-5}$alkyl, wherein the halogen is preferably Cl or F. Most preferably, R$_3$ is H, Cl or methyl; R$_4$ is H, Cl or methyl; R$_5$ is H, F or methyl.

Preferably, in formula (I), R$_2$ is H or methyl.

In formula (I), when Q is CH, X is O, R$_5$ is F; or when Q is N, X is S, R$_5$ is H.

The above benzopyrone derivatives are selected from the following compounds or the pharmaceutically acceptable salts thereof:

7-(4-(4-(3-(6-fluoro-benzisoxazole)-1-piperidyl)-n-butoxy))-2H-benzopyran-2-one;

7-(4-(4-(3-(1,2-benzisothiazole)-1-piperazinyl)-n-butoxy))-2H-benzopyran-2-one;

7-(3-(4-(3-(6-fluoro-benzisoxazole)-1-piperidyl)-n-propoxy))-2H-benzopyran-2-one;

7-(3-(4-(3-(1,2-benzisothiazole)-1-piperazinyl)-n-propoxy))-2H-benzopyran-2-one;

7-(4-(4-(3-(1,2-benzisothiazole)-1-piperazinyl)-n-butoxy))-4-methyl-2H-benzopyran-2-one;

7-(4-(4-(3-(6-fluoro-benzisoxazole)-1-piperidyl)-n-butoxy))-4-methyl-2H-benzopyran-2-one;

7-(3-(4-(3-(6-fluoro-benzisoxazole)-1-piperidyl)-n-propoxy))-4-methyl-2H-benzopyran-2-one;

7-(3-(4-(3-(1,2-benzisothiazole)-1-piperazinyl)-n-propoxy))-4-methyl-2H-benzopyran-2-one;

7-(5-(4-(3-(6-fluoro-benzisoxazole)-1-piperidyl)-n-pentyloxy))-4-methyl-2H-benzopyran-2-one;

(E)-7-(4-(4-(3-(6-fluoro-benzisoxazole)-3-piperidyl)-but-2-enyloxy))-4-methyl-2H-benzopyran-2-one;

7-(3-(4-(3-(1,2-benzisothiazole)-1-piperazinyl)-n-propoxy))-4-phenyl-2H-benzopyran-2-one;

7-(4-(4-(3-(6-fluoro-benzisoxazole)-1-piperidyl)-n-butoxy))-4-phenyl-2H-benzopyran-2-one;

7-(4-(4-(3-(1,2-benzisothiazole)-1-piperazinyl)-n-butoxy))-4-phenyl-2H-benzopyran-2-one;

7-(3-(4-(3-(6-fluoro-benzisoxazole)-1-piperidyl)-n-propoxy))-4-(trifluoromethyl)-2H-benzopyran-2-one;

7-(3-(4-(3-(1,2-benzisothiazole)-1-piperazinyl)-n-propoxy))-4-(trifluoromethyl)-2H-benzopyran-2-one;

7-(4-(4-(3-(6-fluoro-benzisoxazole)-1-piperidyl)-n-butoxy))-4-(trifluoromethyl)-2H-benzopyran-2-one;

7-(4-(4-(3-(1,2-benzisothiazole)-1-piperazinyl)-n-butoxy))-4-(trifluoromethyl)-2H-benzopyran-2-one;

7-(4-(4-(3-(6-fluoro-benzisoxazole)-1-piperidyl)-n-butoxy))-4-methyl-8-chloro-2H-benzopyran-2-one;

7-(4-(4-(3-(1,2-benzisothiazole)-1-piperazinyl)-n-butoxy))-4-methyl-8-chloro-2H-benzopyran-2-one;

7-(3-(4-(3-(6-fluoro-benzisoxazole)-1-piperidyl)-n-propoxy))-4-methyl-8-chloro-2H-benzopyran-2-one;

7-(3-(4-(3-(1,2-benzisothiazole)-1-piperazinyl)-n-propoxy))-4-methyl-8-chloro-2H-benzopyran-2-one;

7-(4-(4-(3-(6-fluoro-benzisoxazole)-1-piperidyl)-n-butoxy))-4,8-dimethyl-2H-benzopyran-2-one;

7-(4-(4-(3-(1,2-benzisothiazole)-1-piperazinyl)-n-butoxy))-4-8-dimethyl-2H-benzopyran-2-one;

7-(4-(4-(3-(6-fluoro-benzisoxazole)-1-piperidyl)-n-butoxy))-4-n-propyl-2H-benzopyran-2-one;

7-(4-(4-(3-(1,2-benzisothiazole)-1-piperazinyl)-n-butoxy))-4-n-propyl-2H-benzopyran-2-one;

7-(4-(4-(3-(6-fluoro-benzisoxazole)-1-piperidyl)-n-butoxy))-4-ethyl-2H-benzopyran-2-one;

7-(4-(4-(3-(1,2-benzisothiazole)-1-piperazinyl)-n-butoxy))-4-ethyl-2H-benzopyran-2-one;

7-(3-(4-(3-(6-fluoro-benzisoxazole)-1-piperidyl)-n-propoxy))-3,4-dimethyl-2H-benzopyran-2-one;

7-(4-(4-(3-(6-fluoro-benzisoxazole)-1-piperidyl)-n-butoxy))-3,4-dimethyl-2H-benzopyran-2-one 7-(3-(4-(3-(6-fluoro-benzisoxazole)-1-piperidyl)-n-propoxy))-4-hydroxymethyl-2H-benzopyran-2-one;

7-(4-(4-(3-(6-fluoro-benzisoxazole)-1-piperidyl)-n-butoxy))-4-hydroxymethyl-2H-benzopyran-2-one;

7-(3-(4-(3-(6-fluoro-benzisoxazole)-1-piperidyl)-2-hydroxylpropoxy))-4-methyl-2H-benzopyran-2-one;

7-(3-(4-(3-(6-fluoro-benzisoxazole)-1-piperidyl)-2-hy-droxylpropoxy))-4-phenyl-2H-benzopyran-2-one; and 7-(4-(4-(3-(6-fluoro-benzisoxazole)-1-piperidyl)-n-pro-poxy))-4-phenyl-benzopyran-2-one.

DETAILED DESCRIPTION OF THE INVENTION

For the purpose of the invention, the term "$C_{1-5}$alkyl" refers to a linear or branched alkyl containing 1, 2, 3, 4, or 5 carbon atoms. For example, $C_{1-5}$alkyl may be methyl, ethyl, n-propyl, isopropyl, n-butyl, isobutyl, t-butyl, n-pentyl, iso-pentyl, neopentyl or the like. The term "$C_{1-5}$alkoxy" refers to the above defined $C_{1-5}$alkyl, which is attached to the rest of the molecule via an oxygen atom.

The term "aromatic ring" refers to an aromatic ring group having 5-14 carbon ring atoms, preferably 5-10 or 6-10 carbon ring atoms, for example, phenyl or naphthyl. Any aryl defined herein may be substituted by one, two or more substituents preferable selected from the group consisting of halogen, hydroxyl, cyano, amino, $C_{1-5}$alkyl (e.g. methyl or ethyl), and $C_1$-$C_5$alkoxy (e.g methoxy).

The term "halogen" refers to F (fluorine), Cl (chlorine), Br (bromine) or I (iodine).

The compound of formula (I) can be reacted with a pharmaceutically acceptable acid to form a pharmaceutically acceptable salt, which may be hydrochloride, hydrobromide, hydriodate, nitrate, sulfate or bisulfate, phosphate or acid phosphate, acetate, lactate, citrate, tartrate, maleate, fumarate, mesylate, gluconate, saccharate, benzoate, ethanesulfonate, benzenesulfonate, p-toluenesulfonate or the like.

The general synthesis procedures of the present compounds can be performed by synthesizing the parent structure of benzopyrone, and then the attaching it to 1,2-benzisox-azole or 1,2-benzisothiazole substituted by a piperazinyl or a piperidyl via a carbon chain. For example, the compounds of the invention can be synthesized according to following Schemes 1-5.

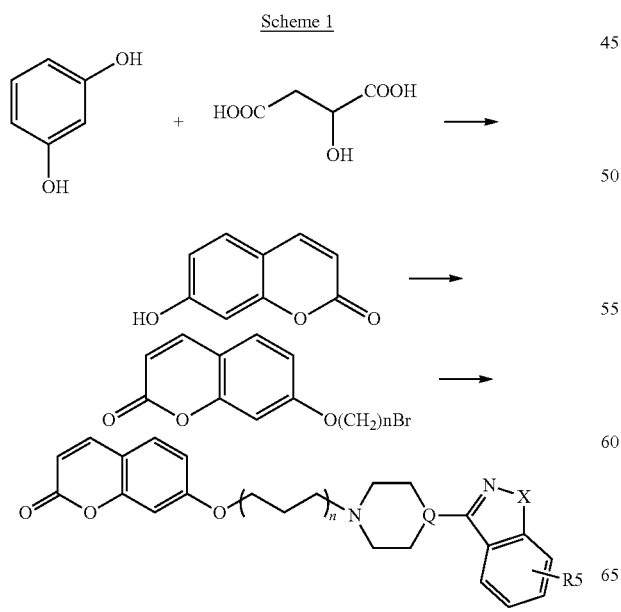

Scheme 1

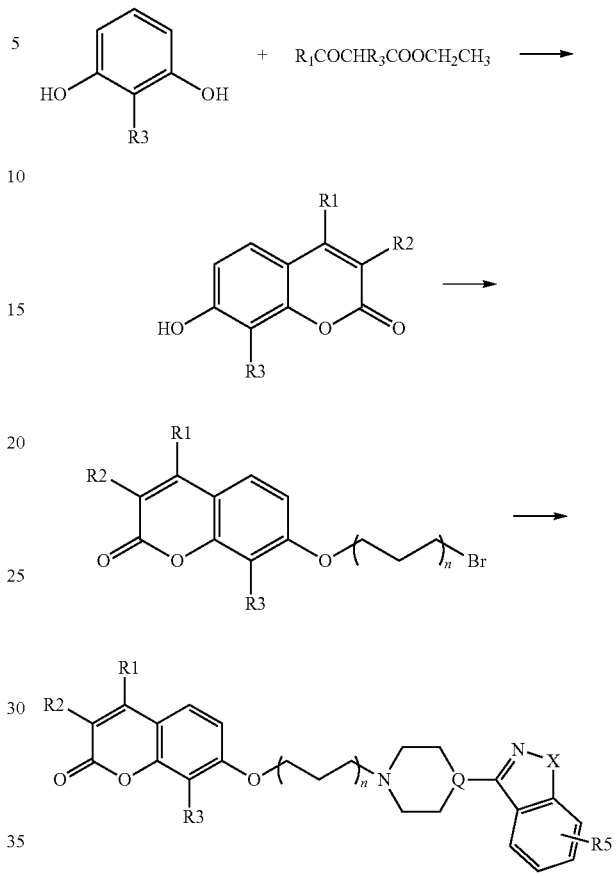

Scheme 2

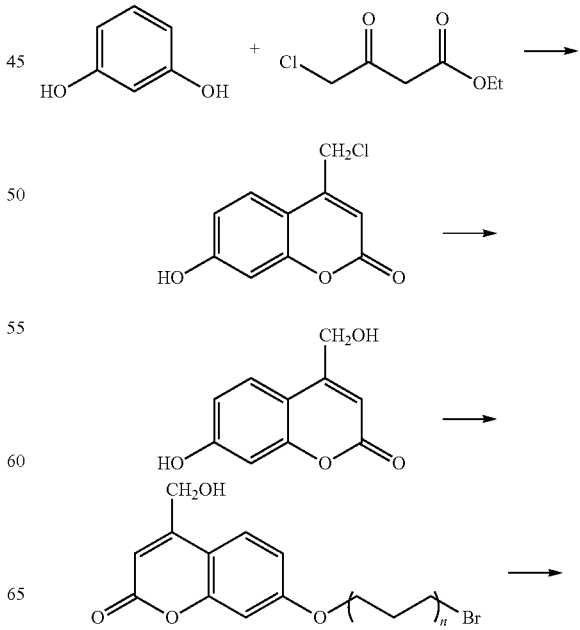

Scheme 3

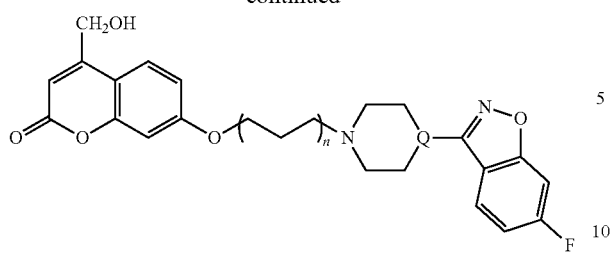

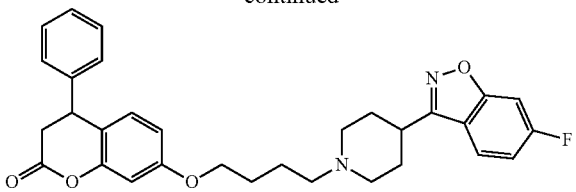

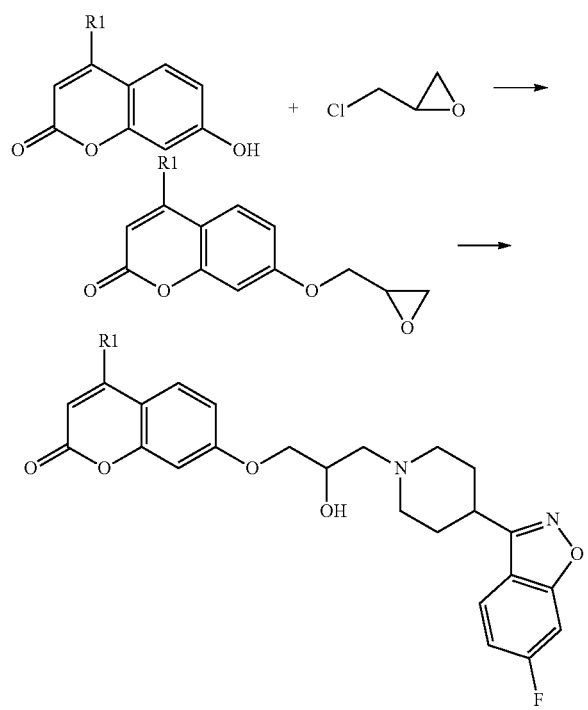

Scheme 4

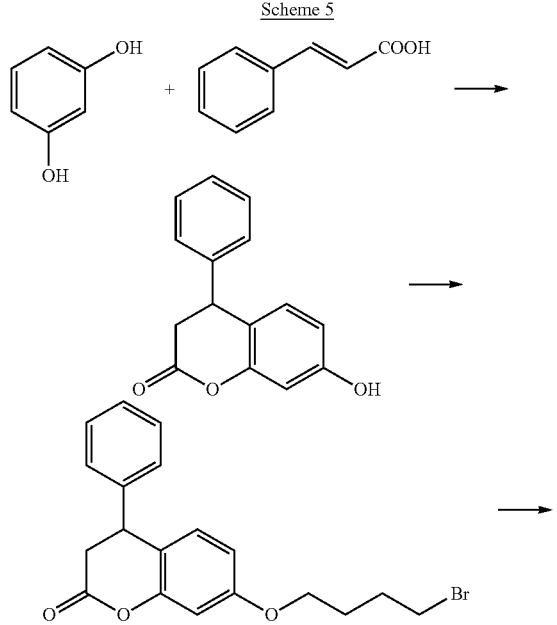

Scheme 5

The invention provides a pharmaceutical composition, comprising the compound of formula (I) or the pharmaceutically acceptable salt thereof, and pharmaceutically acceptable adjuvant (e.g. carrier and/or excipient). This pharmaceutical composition is an anti-psychosis composition comprising the compound according to the invention in an amount sufficient to exert anti-psychosis effect.

The effective dose of the present compounds can be orally administrated with, for example, inert diluent or some carriers. It can be encapsulated in a gelatin capsule or compressed into a tablet. For the purpose of oral administration, the compounds according to the invention can be used with excipients and in the forms of tablet, troche, capsule, suspension, syrup or the like. These formulation should contain the active compounds according to the invention in an amount of at least 0.5 wt %, but such an amount can vary according to particular formulations, and the amount of 4-7% by weight will be beneficial. The active compounds should be present in a suitable dosage in such compositions. The oral unit dose of the preferable composition and formulation contains 1.0-300 mg of the active compounds according to the invention.

The compound provided herein, i.e. the compound of formula (I) and the pharmaceutically acceptable salt, solvate and hydrate thereof can be combined with the pharmaceutically acceptable carrier or diluent to form a pharmaceutical formulation. The pharmaceutically acceptable carrier comprises inert solid filler or diluent and sterile aqueous solution or organic solution.

The dosage of the compound according to the invention depends on the type and severity of the disease or disorder, and the nature of the subject, for example, general health, age, gender, weight and drug tolerance. A person skilled in the art can determine the suitable dosage according to these or other factors. The effective dosage for a central nervous system drug is well known to a person skilled in the art. The total daily dosage is generally about 0.05 mg-2000 mg.

The invention relates to a pharmaceutical composition, which can provide about 0.01-1000 mg active ingredient per unit dose. The composition can be administrated in any suitable route, for example, oral administration in a capsule, parenteral administration in an injection, topical administration in an ointment or a lotion, rectal administration in a suppository, or transdermal administration in a patch.

The compounds according to the invention can be combined with suitable solid or liquid carrier or diluent to form capsule, tablet, pill, powder, syrup, solution or the like. The tablet, pill, capsule or the like contains about 0.01% to about 99% by weight of active ingredients and binder, such as gelatin, maize starch, arabic gum etc; excipient, such as calcium hydrophosphate; disintegrant, such as maize starch, potato starch or alginic acid; lubricant, such as magnesium stearate; and sweetener, such as sucrose, lactose. When the formulation is in the form of capsule, in addition to above materials, it may contain liquid carrier, for example, grease.

For the parenteral administration, the compounds according to the invention can be combined with sterile water or organic medium to form injectable solution or suspension.

The compounds according to the invention may contain a chiral center(s), thereby being present in the form of different enantiomers or diastereomers. Accordingly, the invention relates to all the optical isomers and all the stereoisomers of the present compounds, in the forms of racemic mixture and respective enantiomers and diastereomers. Moreover, the invention relates to the above defined compounds or all the pharmaceutical compositions containing or using the same as well as the therapeutical method using the same.

Furthermore, the compounds according to the invention and the pharmaceutical composition containing the same may be used to prepare a medicament for the treatment or prevention of a neuropsychical disease selected from the group consisting of mental disorder, anxiety, personality disorder, depression, mania, migraine, epilepsy or spasticity disorder, childhood disorder, Parkinson's disease, cognitive disorder, neural degeneration, neurotoxicity and ischemia, preferably schizophrenia. The compounds according to the invention may also be used to prepare a medicament for the treatment or prevention of other central nervous system diseases, for example, depression, memory disorder and functional disorders associated with intelligence, learning or the like.

It is shown in the in vitro receptor binding assay that the derivates according to the invention have relatively high affinities for dopamine $D_2$, $D_3$, $5\text{-}HT_{1A}$ and $5\text{-}HT_{2A}$ receptors, while low affinities for $5\text{-}HT_{2C}$.

It is shown in the animal experiments that these compounds can significantly improve the MK-801 induced high activity and effectively improve the apomorphine induced clambering symptoms, without causing EPS at effective dosage. Since these in vitro acting targets and in vivo pharmacological models are closely associated with dopamine function disorder induced neural system disease, particularly schizophrenia, the compounds according to the invention have the therapeutic effect for neuropsychical disease, especially schizophrenia.

EXAMPLES

The following Examples are provided for illustrative purposes rather than limiting to the invention.
A. Synthetic Examples Example 1

7-(4-(4-(3-(6-fluoro-benzisoxazole)-1-piperidyl)-n-butoxy))-2H-benzopyran-2-one (1)

The target compound was synthesized according to Scheme 1.
1) 5.5 g of resorcinol and 6.7 g of d,l-malic acid were added to 50 ml of 70% $HClO_4$, and the solution was heated to 90° C. for reaction. The solution became clear slowly, and the reaction was completed after 4 hours. The reaction mixture was cooled to room temperature, and the reaction liquid was poured into an ice-water mixture. A large amount of solid was precipitated, which were filtrated. The cake was washed with water. Recrystallization with 95% ethanol gave 4.5 g of white crystal. Melting point: 226-228° C., Yield: 60.8%.
2) 5 g of product of step 1), 6 g of anhydrous potassium carbonate, 50 ml of acetone and 8.2 g of 1,4-dibromobutane were heated under reflux for 6 hours. Then the mixture was cooled to room temperature and filtrated. The solvent was distilled to give yellowish oil, which was passed through a column to give 5.4 g of white solid. Melting point: 55-57° C., Yield: 60.7%.
3) 0.52 g of the product of step 2), 0.65 g of 6-fluoro-3-(4-piperidyl)-1,2-benzisoxazole hydrochloride, 2 g of anhydrous potassium carbonate, 0.2 g of potassium iodide and 25 ml of acetonitrile were heated under reflux for 12 hours. Then the mixture was cooled to room temperature, and the solvent was distilled. A suitable amount of dichloromethane was added to the mixture, which was then washed with water. The aqueous layer was discarded, and to the organic layer was added anhydrous magnesium sulfate for drying. The solvent was distilled to give yellowish oil. Column chromatography gave 0.55 g of white solid. Melting point: 116-118° C., Yield: 72.3%.

$^1$H NMR (CDCl$_3$) δ 1.73-1.88 (m, 4H), 2.06-2.16 (m, 6H), 2.48 (t, 2H, J=14.4 Hz), 3.07-3.10 (m, 4H), 4.07 (t, 2H, J=12 Hz), 6.24 (d, 1H, J=9.6 Hz), 6.80-6.86 (m, 2H), 7.05 (t, 1H, J=1.6 Hz), 7.22-7.24 (m, 1H), 7.37 (d, 1H, J=8.4 Hz), 7.63-7.69 (m, 2H)

MS (ESI) m/z 437.2 ([M+H]$^+$)

Example 2

7-(4-(4-(3-(1,2-benzisothiazole)-1-piperazinyl)-n-butoxy))-2H-benzopyran-2-one (2)

The target compound was prepared according to the procedures of Example 1, using 3-(1-piperazinyl)-1,2-benzisothiazole hydrochloride instead of 6-fluoro-3-(4-piperidyl)-1,2-benzisoxazole hydrochloride.

Melting point 103-105° C.

$^1$H NMR (CDCl$_3$) δ 1.75-1.76 (m, 2H), 1.87-1.91 (m, 2H), 2.51 (t, 2H, J=14.8 Hz), 2.68-2.71 (m, 4H), 3.56-3.59 (m, 4H), 4.06 (t, 2H, J=12.4 Hz), 6.23 (d, 1H, J=9.6 Hz), 6.80-6.85 (m, 2H), 7.33-7.37 (m, 2H), 7.44-7.48 (m, 1H), 7.62 (d, 1H, J=9.6 Hz), 7.80 (d, 1H, J=8 Hz), 7.91 (d, 1H, J=8 Hz)

MS (ESI) m/z 436.2 ([M+H]$^+$)

Example 3

7-(3-(4-(3-(6-fluoro-benzisoxazole)-1-piperidyl)-n-propoxy))-2H-benzopyran-2-one (3)

The target compound was prepared according to the procedures of Example 1, using 1,3-dibromopropane instead of 1,4-dibromobutane.

Melting point: 128-130° C.

$^1$H NMR (CDCl$_3$) δ 2.03-2.19 (m, 8H), 2.60 (t, 2H, J=14.4 Hz), 3.07-3.10 (m, 3H), 4.12 (t, 2H, J=12.8 Hz), 6.25 (d, 1H, J=9.2 Hz), 6.84-6.87 (m, 2H), 7.05-7.06 (m, 1H), 7.23-7.27 (m, 1H), 7.37 (d, 1H, J=8.4 Hz), 7.63-7.70 (m, 2H)

MS (ESI) m/z 423.2 ([M+H]$^+$)

Example 4

7-(3-(4-(3-(1,2-benzisothiazole)-1-piperazinyl)-n-propoxy))-2H-benzopyran-2-one (4)

The target compound was prepared according to the procedures of Example 1, using 1,3-dibromopropane instead of 1,4-dibromobutane.

Melting point: 91-93° C.

$^1$H NMR (CDCl$_3$) δ 2.04-2.08 (m, 2H), 2.64 (t, 2H, J=14.4 Hz), 2.70-2.73 (m, 4H), 3.57-3.59 (m, 4H), 4.12 (t, 2H, J=12.8 Hz), 6.23 (d, 1H, J=9.6 Hz), 6.82-6.86 (m, 2H), 7.33-7.37 (m, 2H), 7.44-7.48 (m, 1H), 7.62 (d, 1H, J=9.6 Hz), 7.80 (d, 1H, J=8 Hz), 7.91 (d, 1H, J=8 Hz)

MS (ESI) m/z 422.2 ([M+H]$^+$)

Example 5

7-(4-(4-(3-(1,2-benzisothiazole)-1-piperazinyl)-n-butoxy))-4-methyl-2H-benzopyran-2-one (5)

The target compound was synthesized according to Scheme 2.

1) 30 ml of concentrated sulfuric acid was stirred in an ice bath, to which was added resorcinol (5.5 g), and ethyl acetoacetate (9.2 g) dropwise. The solution turned yellow from yellowish, and the reaction was completed after 18 hours. The reaction liquid was poured into ice/water mixture, and white solid was precipitated, which was filtrated. The cake was washed with water to neutral. Recrystallization with 75% ethanol gave 8.5 g of white crystal. Melting point: 186-188° C., yield: 73.9%.

2) 5 g of the product of step 1), 6 g of anhydrous potassium carbonate, 50 ml of acetone and 8.7 g of 1,4-dibromobutane were heated under reflux for 4 hours, and then cooled to room temperature. The mixture was filtrated and the solvent was distilled to give yellowish oil, which was passed through a column to give 6.5 g of white solid. Melting point: 58-60° C., yield: 77.8%.

3) To 0.5 g of the product of step 2) were added 0.6 g of 3-(1-piperazinyl)-1,2-benzisothiazole hydrochloride, 2 g of anhydrous potassium carbonate, 0.2 g of potassium iodide and 25 ml of acetonitrile, and the mixture was heated under reflux for 20 hours, and then cooled to room temperature and filtrated. The solvent was distilled to give yellowish oil, which was passed through a column to give 0.52 g of white solid. Melting point: 110-112° C., yield: 72.2%.

$^1$H NMR (CDCl$_3$) δ 1.75-1.90 (m, 4H), 2.38 (s, 3H), 2.51 (t, 2H, J=14.4 Hz), 2.68-2.71 (m, 4H), 3.56-3.58 (m, 4H), 4.06 (t, 2H, J=12 Hz), 6.11 (s, 1H), 6.80-6.86 (m, 2H), 7.29-7.36 (m, 1H), 7.43-7.48 (m, 2H), 7.79 (d, 1H, J=8 Hz), 7.90 (d, 1H, J=8.4 Hz)

MS (ESI) m/z 450.2 ([M+H]$^+$)

Example 6

7-(4-(4-(3-(6-fluoro-benzisoxazole)-1-piperidyl)-n-butoxy))-4-methyl-2H-benzopyran-2-one (6)

The target compound was prepared according to the procedures of Example 5, using 6-fluoro-3-(4-piperidyl)-1,2-benzisoxazole hydrochloride instead of 3-(1-piperazinyl)-1,2-benzisothiazole hydrochloride.

Melting point: 126-128° C.

$^1$H NMR (CDCl$_3$) δ 1.71-1.92 (m, 4H), 2.09-2.19 (m, 6H), 2.09 (s, 3H), 2.50 (t, 2H, J=14.4 Hz), 3.09-3.12 (m, 3H), 4.07 (t, 2H, J=12.8 Hz), 6.13 (s, 1H), 6.81-6.88 (m, 2H), 7.03-7.08 (m, 1H), 7.23-7.25 (m, 1H), 7.49 (d, 1H, J=8.8 Hz), 7.69-7.72 (m, 1H)

MS (ESI) m/z 451.3 ([M+H]$^+$)

Example 7

7-(3-(4-(3-(6-fluoro-benzisoxazole)-1-piperidyl)-n-propoxy))-4-methyl-2H-benzopyran-2-one (7)

The target compound was prepared according to the procedures of Example 6, using 1,3-dibromopropane instead of 1,4-dibromobutane.

Melting point: 138-140° C.

$^1$H NMR (CDCl$_3$) δ 2.02-2.23 (m, 8H), 2.40 (s, 3H), 2.60 (t, 2H, J=14.4 Hz), 3.07-3.10 (m, 3H), 4.12 (t, 2H, J=12.8 Hz), 6.13 (s, 1H), 6.84-6.89 (m, 2H), 7.06 (t, 1H, J=2 Hz), 7.23-7.27 (m, 1H), 7.50 (d, 1H, J=8.8 Hz), 7.71 (t, 1H, J=8.8 Hz)

MS (ESI) m/z 437.2 ([M+H]$^+$)

Example 8

7-(3-(4-(3-(1,2-benzisothiazole)-1-piperazinyl)-n-propoxy))-4-methyl-2H-benzopyran-2-one (8)

The target compound was prepared according to the procedures of Example 5, using 1,3-dibromopropane instead of 1,4-dibromobutane.

Melting point: 113-115° C.

$^1$H NMR (CDCl$_3$) δ 2.06-2.08 (m, 2H), 2.38 (s, 3H), 2.64 (t, 2H, J=14.4 Hz), 2.70-2.73 (m, 4H), 3.57-3.59 (m, 4H), 4.12 (t, 2H, J=12.4 Hz), 6.12 (s, 1H), 6.82-6.88 (m, 2H), 7.35-7.49 (m, 3H), 7.80 (d, 1H, J=8 Hz), 7.91 (d, 1H, J=8.4 Hz)

MS (ESI) m/z 436.2 ([M+H]$^+$)

Example 9

7-(5-(4-(3-(6-fluoro-benzisoxazole)-1-piperidyl)-n-pentyloxy))-4-methyl-2H-benzopyran-2-one (9)

The target compound was prepared according to the procedures of Example 6, using 1,5-dibromopentane instead of 1,4-dibromobutane.

Melting point: 119-121° C.

$^1$H NMR (CDCl$_3$) δ 1.53-1.63 (m, 4H), 1.85-1.89 (m, 2H), 2.05-2.14 (m, 6H), 2.40 (s, 3H), 2.43 (t, 2H, J=14.8 Hz), 3.06-3.08 (m, 3H), 4.04 (t, 2H, J=12.8 Hz), 6.12 (s, 1H), 6.80-6.87 (m, 2H), 7.02-7.07 (m, 1H), 7.22-7.24 (m, 1H), 7.49 (d, 1H, J=4.8 Hz), 7.67-7.71 (m, 1H)

MS (ESI) m/z 465.3 ([M+H]$^+$)

Example 10

(E)-7-(4-(4-(3-(6-fluoro-benzisoxazole)-3-piperidyl)-but-2-enyloxy))-4-methyl-2H-benzopyran-2-one (10)

The target compound was prepared according to the procedures of Example 6, using 1,4-dibromo-2-butene instead of 1,4-dibromobutane.

Melting point: 129-130° C.

$^1$H NMR (CDCl$_3$) δ 2.05-2.17 (m, 6H), 2.39 (s, 3H), 3.05-3.13 (m, 5H), 4.06 (t, 2H, J=12.8 Hz), 5.91-5.96 (m, 2H), 6.13 (s, 1H), 6.83-6.90 (m, 1H), 7.05-7.06 (m, 1H), 7.22-7.27 (m, 1H), 7.49 (d, 1H, J=8.8 Hz), 7.68-7.70 (m, 1H)

MS (ESI) m/z 449.2 ([M+H]$^+$)

Example 11

7-(3-(4-(3-(6-fluoro-benzisoxazole)-1-piperidyl)-n-propoxy))-4-phenyl-2H-benzopyran-2-one (11)

1) To 5.5 g of resorcinol and 9.6 g of ethyl benzoylacetate was added 30 ml of phosphoric acid, and the mixture was stirred under room temperature. The solution turned yellow from yellowish, and the reaction was completed after 12 hours. The reaction liquid was poured into ice/water mixture, and a lot of solid was precipitated, which was filtrated. The cake was washed with water. Recrystallization with 95% ethanol gave 9.3 g of white crystal. Melting point: 237-239° C., yield: 80.9%.

2) 4.8 g of the product of step 1), 6 g of anhydrous potassium carbonate, 50 ml of acetone and 8.4 g of 1,3-dibromopropane were heated under reflux for 4 hours, and then cooled to room temperature and filtrated. The solvent was removed by rotation and the residue was passed through a column to give 5.6 g of white solid. Melting point: 67-69° C., yield: 78.0%.

3) To 0.5 g of the product of step 2) were added 0.6 g of 6-fluoro-3-(4-piperidyl)-1,2-benzisoxazole hydrochloride, 2 g of anhydrous potassium carbonate, 0.2 g of potassium iodide and 25 ml acetonitrile, and the mixture was heated under reflux for 24 hours and then cooled to room temperature and filtrated. The solvent was distilled to give yellowish oil, which was passed through a column to give 0.51 g of white solid. Melting point: 185-187° C., yield: 73.9%.

$^1$H NMR (CDCl$_3$) δ 2.04-2.19 (m, 8H), 2.67-2.77 (m, 6H), 3.07-3.10 (m, 3H), 4.13 (t, 2H, J=12.4 Hz), 6.22 (s, 1H), 6.79-6.82 (m, 1H), 6.91-6.92 (m, 1H), 7.05-7.06 (m, 1H), 7.23-7.27 (m, 1H), 7.37-7.51 (m, 6H), 7.68-7.71 (m, 1H)

MS (ESI) m/z 499.3 ([M+H]$^+$)

Example 12

7-(3-(4-(3-(1,2-benzisothiazole)-1-piperazinyl)-n-propoxy))-4-phenyl-2H-benzopyran-2-one (12)

The target compound was prepared according to the procedures of Example 11, using 3-(1-piperazinyl)-1,2-benzisothiazole hydrochloride instead of 6-fluoro-3-(4-piperidyl)-1,2-benzisoxazole hydrochloride.

Melting point: 96-98° C.

$^1$H NMR (CDCl$_3$) δ 2.05-2.08 (m, 2H), 2.62-2.72 (m, 6H), 3.57-3.59 (m, 4H), 4.13 (t, 2H, J=14 Hz), 6.20 (s, 1H), 6.79-6.82 (m, 2H), 6.90 (d, 1H, J=2 Hz), 7.36-7.51 (m, 8H), 7.81 (d, 1H, J=8 Hz), 7.92 (d, 1H, J=8 Hz)

MS (ESI) m/z 498.3 ([M+H]$^+$)

Example 13

7-(4-(4-(3-(6-fluoro-benzisoxazole)-1-piperidyl)-n-butoxy))-4-phenyl-2H-benzopyran-2-one (13)

The target compound was prepared according to the procedures of Example 11, using 1,4-dibromobutane instead of 1,3-dibromopropane.

Melting point: 97-99° C.

$^1$H NMR (CDCl$_3$) δ 1.72-1.76 (m, 2H), 1.87-1.91 (m, 2H), 2.07-2.18 (m, 6H), 2.48 (t, 2H, J=14.8 Hz), 3.07-3.10 (m, 3H), 4.08 (t, 2H, J=12.4 Hz), 6.21 (s, 1H), 6.80-6.81 (m, 1H), 6.88-6.89 (m, 1H), 7.03-7.07 (m, 1H), 7.21-7.24 (m, 1H), 7.37-7.52 (m, 6H), 7.68-7.71 (m, 1H)

MS (ESI) m/z 4514.3 ([M+H]$^+$)

Example 14

7-(4-(4-(3-(1,2-benzisothiazole)-1-piperazinyl)-n-butoxy))-4-phenyl-2H-benzopyran-2-one (14)

The target compound was prepared according to the procedures of Example 12, using 1,4-dibromobutane instead of 1,3-dibromopropane.

Melting point: 116-118° C.

$^1$H NMR (CDCl$_3$) δ 1.76-1.90 (m, 4H), 2.53 (t, 2H, J=14.8 Hz), 2.70-2.72 (m, 4H), 3.57-3.59 (m, 4H), 4.09 (t, 2H, J=12.4 Hz), 6.21 (s, 1H), 6.78-6.80 (m, 1H), 6.89 (d, 1H, J=2.4 Hz), 7.35-7.52 (m, 8H), 7.81 (d, 1H, J=8 Hz), 7.91 (d, 1H, J=8.4 Hz)

MS (ESI) m/z 512.3 ([M+H]$^+$)

Example 15

7-(3-(4-(3-(6-fluoro-benzisoxazole)-1-piperidyl)-n-propoxy))-4-(trifluoromethyl)-2H-benzopyran-2-one (15)

1) 30 ml of concentrated sulfuric acid was stirred in an ice bath, to which was added 5.5 g of resorcinol and was added 9.2 g of trifluoro ethyl acetoacetate dropwise. The solution turned yellow from yellowish. The reaction was carried out for 18 hours. The reaction liquid was poured into ice/water mixture, and a lot of solid was precipitated, which was filtrated. The cake was washed with water to neutral. Recrystallization with 75% ethanol gave 8.5 g of white crystal. Melting point: 218-220° C., yield: 73.9%.

2) 4.6 g of the product of step 1), 6 g of anhydrous potassium carbonate, 50 ml of acetone and 8.4 g of 1,3-dibromopropane were heated under reflux for 4 hours, and then cooled to room temperature and filtrated. The solvent was removed by rotation to give yellowish oil, which was passed through a column to give 5.6 g of white solid. Melting point: 72-74° C., yield: 80.1%.

3) To 0.5 g of the product of step 2) were added 0.6 g of 6-fluoro-3-(4-piperidyl)-1,2-benzisoxazole hydrochloride, 2 g of anhydrous potassium carbonate, 0.2 g of potassium iodide and 25 ml of acetonitrile, and the mixture was heated under reflux for 12 hours, and then cooled to room temperature and filtrated. The solvent was removed by rotation to give yellowish oil, which was passed through a column to give 0.50 g of white solid. Melting point: 146-148° C., yield: 71.4%.

$^1$H NMR (CDCl$_3$) δ 2.04-2.23 (m, 8H), 2.60 (t, 2H, J=6.8 Hz), 3.07-3.13 (m, 3H), 4.15 (t, 2H, J=12.8 Hz), 6.12 (s, 1H), 6.90-6.95 (m, 2H), 7.03-7.08 (m, 1H), 7.23-7.26 (m, 1H), 7.61-7.71 (m, 2H)

MS (ESI) m/z 491.3 ([M+H]$^+$)

Example 16

7-(3-(4-(3-(1,2-benzisothiazole)-1-piperazinyl)-n-propoxy))-4-(trifluoromethyl)-2H-benzopyran-2-one (16)

The target compound was prepared according to the procedures of Example 15, using 3-(1-piperazinyl)-1,2-benzisothiazole hydrochloride instead of 6-fluoro-3-(4-piperidyl)-1,2-benzisoxazole hydrochloride.

Melting point: 103-105° C.

$^1$H NMR (CDCl$_3$) δ 2.10-2.13 (m, 2H), 2.67-2.77 (m, 6H), 3.62 (br, 4H), 4.16 (t, 2H, J=12.4 Hz), 6.62 (s, 1H), 6.90-6.95 (m, 2H), 7.36-7.38 (m, 1H), 7.46-7.47 (m, 1H), 7.61-7.62 (m, 1H), 7.63-7.64 (m, 1H), 7.81-7.90 (m, 1H)

MS (ESI) m/z 490.2 ([M+H]$^+$)

Example 17

7-(4-(4-(3-(6-fluoro-benzisoxazole)-1-piperidyl)-n-butoxy))-4-(trifluoromethyl)-2H-benzopyran-2-one (17)

The target compound was prepared according to the procedures of Example 15, using 1,4-dibromobutane instead of 1,3-dibromopropane.

Melting point: 125-127° C.

$^1$H NMR (CDCl$_3$) δ 1.77-1.92 (m, 4H), 2.11-2.23 (m, 6H), 2.52 (t, 2H, J=14.8 Hz), 3.10-3.13 (m, 3H), 4.10 (t, 2H, J=12.4

Hz), 6.61 (s, 1H), 6.87-6.93 (m, 2H), 7.03-7.08 (m, 1H), 7.22-7.25 (m, 1H), 7.60-7.63 (m, 1H), 7.70-7.73 (m, 1H)
MS (ESI) m/z 505.3 ([M+H]$^+$)

Example 18

7-(4-(4-(3-(1,2-benzisothiazole)-1-piperazinyl)-n-butoxy))-4-(trifluoromethyl)-2H-benzopyran-2-one (18)

The target compound was prepared according to the procedures of Example 16, using 1,4-dibromobutane instead of 1,3-dibromopropane.
Melting point: 93-95° C.
$^1$H NMR (CDCl$_3$) δ 1.76-1.77 (m, 2H), 1.89-1.91 (m, 2H), 2.52 (t, 2H, J=14.8 Hz), 2.70 (t, 4H, J=9.6 Hz), 3.58 (t, 4H, J=9.6 Hz), 4.10 (t, 2H, J=12.4 Hz), 6.61 (s, 1H), 6.87 (d, 1H, J=2.4 Hz), 6.90-6.93 (m, 1H), 7.35 (t, 1H, J=15.2 Hz), 7.46 (t, 1H, J=14.8 Hz), 7.61 (d, 1H, J=1.2 Hz), 7.63 (d, 1H, J=1.2 Hz)
MS (ESI) m/z 504.3 ([M+H]$^+$)

Example 19

7-(4-(4-(3-(6-fluoro-benzisoxazole)-1-piperidyl)-n-butoxy))-4-methyl-8-chloro-2H-benzopyran-2-one (19)

The target compound was prepared according to the procedures of Example 6, using 2-chlororesorcinol as starting material.
Melting point: 128-130° C.
$^1$H NMR (CDCl$_3$) δ 1.78-1.80 (m, 2H), 1.93-2.15 (m, 8H), 2.41 (s, 3H), 2.50 (t, 2H, J=14.4 Hz), 3.07-3.10 (m, 3H), 4.19 (t, 2H, J=12.4 Hz), 6.15 (s, 1H), 6.92 (d, 1H, J=8.8 Hz), 7.02-7.07 (m, 1H), 7.22-7.28 (m, 1H), 7.46 (d, 1H, J=8.8 Hz), 7.68-7.71 (m, 1H)
MS (ESI) m/z 485.2 ([M+H]$^+$)

Example 20

7-(4-(4-(3-(1,2-benzisothiazole)-1-piperazinyl)-n-butoxy))-4-methyl-8-chloro-2H-benzopyran-2-one (20)

The target compound was prepared according to the procedures of Example 5, using 2-chlororesorcinol as starting material.
Melting point: 133-135° C.
$^1$H NMR (CDCl$_3$) δ 1.79-1.85 (m, 2H), 1.93-1.98 (m, 2H), 2.39 (s, 3H), 2.55 (t, 2H, J=7.2 Hz), 2.72 (t, 2H, J=9.6 Hz), 3.58 (t, 4H, J=9.6 Hz), 4.18 (t, 2H, J=12.4 Hz), 6.14 (s, 1H), 6.88-6.91 (m, 1H), 7.33-7.37 (m, 1H), 7.43-7.48 (m, 2H), 7.80 (d, 1H, J=8.4 Hz), 7.90 (d, 1H, J=8 Hz)
MS (ESI) m/z 484.2 ([M+H]$^+$)

Example 21

7-(3-(4-(3-(6-fluoro-benzisoxazole)-1-piperidyl)-n-propoxy))-4-methyl-8-chloro-2H-benzopyran-2-one (21)

The target compound was prepared according to the procedures of Example 7, using 2-chlororesorcinol as starting material.
Melting point: 185-187° C.
$^1$H NMR (CDCl$_3$) δ 2.07-2.20 (m, 8H), 2.41 (s, 3H), 2.64 (t, 2H, J=7.2 Hz), 3.08-3.10 (m, 3H), 4.24 (t, 2H, J=12 Hz), 6.17 (s, 1H), 6.94 (d, 1H, J=8.8 Hz), 7.05 (t, 1H, J=2 Hz), 7.25 (t, 1H, J=16 Hz), 7.46 (d, 1H, J=8.8 Hz), 7.66-7.70 (m, 1H)
MS (ESI) m/z 471.2 ([M+H]$^+$)

Example 22

7-(3-(4-(3-(1,2-benzisothiazole)-1-piperazinyl)-n-propoxy))-4-methyl-8-chloro-2H-benzopyran-2-one (22)

The target compound was prepared according to the procedures of Example 8, using 2-chlororesorcinol as starting material.
Melting point: 162-164° C.
$^1$H NMR (CDCl$_3$) δ 1.79-1.98 (m, 4H), 2.39 (s, 3H), 2.55 (t, 2H, J=7.2 Hz), 2.72 (t, 4H, J=9.6 Hz), 3.58 (t, 4H, J=9.6 Hz), 4.18 (t, 2H, J=12.4 Hz), 6.14 (s, 1H), 6.90 (d, 1H, J=8.8 Hz), 7.35 (t, 1H, J=14.8 Hz), 7.43-7.48 (m, 2H), 7.80 (d, 1H, J=8.4 Hz), 7.90 (d, 1H, J=8 Hz)
MS (ESI) m/z 470.2 ([M+H]$^+$)

Example 23

7-(4-(4-(3-(6-fluoro-benzisoxazole)-1-piperidyl)-n-butoxy))-4,8-dimethyl-2H-benzopyran-2-one (23)

The target compound was prepared according to the procedures of Example 6, using 2-methylresorcinol as starting material.
Melting point: 117-119° C.
$^1$H NMR (CDCl$_3$) δ 1.72-1.80 (m, 2H), 1.88-1.94 (m, 2H), 2.05-2.19 (m, 6H), 2.31 (s, 3H), 2.39 (s, 3H), 2.49 (t, 2H, J=14.8 Hz), 3.09 (d, 3H, J=10 Hz), 4.11 (t, 2H, J=12.4 Hz), 6.11 (s, 1H), 6.84 (d, 1H, J=8.8 Hz), 7.05 (t, 1H, J=2 Hz), 7.22-7.24 (m, 1H), 7.40 (d, 1H, J=8.8 Hz), 7.68-7.71 (m, 1H)
MS (ESI) m/z 465.3 ([M+H]$^+$)

Example 24

7-(4-(4-(3-(1,2-benzisothiazole)-1-piperazinyl)-n-butoxy))-4-8-dimethyl-2H-benzopyran-2-one (24)

The target compound was prepared according to the procedures of Example 5, using 2-methylresorcinol as starting material.
Melting point: 106-108° C.
$^1$H NMR (CDCl$_3$) δ 1.73-1.86 (m, 4H), 2.05-2.17 (m, 9H), 2.36 (s, 3H), 2.48 (t, 2H, J=14.8 Hz), 3.07-3.10 (m, 3H), 4.05 (t, 2H, J=12.4 Hz), 6.78-6.86 (m, 2H), 7.02-7.07 (m, 1H), 7.21-7.24 (m, 1H), 7.48 (d, 1H, J=8.8 Hz), 7.68-7.71 (m, 1H)
MS (ESI) m/z 464.3 ([M+H]$^+$)

Example 25

7-(4-(4-(3-(6-fluoro-benzisoxazole)-1-piperidyl)-n-butoxy))-4-n-propyl-2H-benzopyran-2-one (25)

The target compound was prepared according to the procedures of Example 6, using ethyl butyrylacetate as starting material.
Melting point: 139-141° C.
$^1$H NMR (CDCl$_3$) δ 1.00 (t, 3H, J=14.4 Hz), 1.64-1.69 (m, 2H), 1.93-2.22 (m, 6H), 2.64 (t, 2H, J=14.4 Hz), 3.00-3.74 (m, 9H), 4.04 (t, 2H, J=12.8 Hz), 6.05 (s, 1H), 6.71-6.78 (m, 2H), 7.05-7.23 (m, 2H), 7.80 (d, 1H, J=8 Hz), 7.91 (d, 1H, J=8 Hz)
MS (ESI) m/z 479.3 ([M+H]$^+$)

Example 26

7-(4-(4-(3-(1,2-benzisothiazole)-1-piperazinyl)-n-butoxy))-4-n-propyl-2H-benzopyran-2-one (26)

The target compound was prepared according to the procedures of Example 5, using ethyl butyrylacetate as starting material.

Melting point: 114-116° C.

$^1$H NMR (CDCl$_3$) δ 1.04 (t, 3H, J=14.4 Hz), 1.69-1.90 (m, 6H), 2.51 (t, 2H, J=14.8 Hz), 2.67-2.71 (m, 6H), 3.56-3.58 (m, 4H), 4.06 (t, 2H, J=12.8 Hz), 6.11 (s, 1H), 6.81-6.86 (m, 2H), 7.28-7.52 (m, 3H), 7.80 (d, 1H, J=8 Hz), 7.91 (d, 1H, J=8 Hz)

MS (ESI) m/z 478.3 ([M+H]$^+$)

Example 27

7-(4-(4-(3-(6-fluoro-benzisoxazole)-1-piperidyl)-n-butoxy))-4-ethyl-2H-benzopyran-2-one (27)

The target compound was prepared according to the procedures of Example 6, using ethyl propionylacetate as starting material.

Melting point: 96-98° C.

$^1$H NMR (CDCl$_3$) δ 1.32 (t, 3H, J=14.8 Hz), 1.74-1.90 (m, 4H), 2.06-2.16 (m, 6H), 2.48 (t, 2H, J=14.8 Hz), 2.75-2.81 (m, 2H), 3.05-3.10 (m, 3H), 4.07 (t, 2H, J=12.8 Hz), 6.14 (s, 1H), 6.82-6.87 (m, 2H), 7.03-7.07 (m, 1H), 7.23-7.25 (m, 1H), 7.52 (d, 1H, J=8.8 Hz), 7.68-7.71 (m, 1H)

MS (ESI) m/z 465.3 ([M+H]$^+$)

Example 28

7-(4-(4-(3-(1,2-benzisothiazole)-1-piperazinyl)-n-butoxy))-4-ethyl-2H-benzopyran-2-one (28)

The target compound was prepared according to the procedures of Example 5, using ethyl propionylacetate as starting material.

Melting point: 110-112° C.

$^1$H NMR (CDCl$_3$) δ 1.32 (t, 3H, J=14.8 Hz), 1.76-1.91 (m, 4H), 2.53 (t, 2H, J=14.4 Hz), 2.71-2.79 (m, 6H), 3.58 (br, 4H), 0.07 (t, 2H, J=12.4 Hz), 6.15 (s, 1H), 6.82-6.87 (m, 2H), 7.36 (t, 1H, J=14.8 Hz), 7.47 (t, 1H, J=14.8 Hz), 7.52 (d, 1H, J=8.8 Hz), 7.81 (d, 1H, J=8.4 Hz), 7.91 (d, 1H, J=8 Hz)

MS (ESI) m/z 464.3 ([M+H]$^+$)

Example 29

7-(4-(4-(3-(6-fluoro-benzisoxazole)-1-piperidyl)-n-butoxy))-3,4-dimethyl-2H-benzopyran-2-one (29)

The target compound was prepared according to the procedures of Example 6, using 2-methyl ethyl acetoacetate as starting material.

Melting point: 106-108° C.

$^1$H NMR (CDCl$_3$) δ 1.73-1.86 (m, 4H), 2.05-2.17 (m, 9H), 2.36 (s, 3H), 2.48 (t, 2H, J=14.8 Hz), 3.07-3.10 (m, 3H), 4.05 (t, 2H, J=12.4 Hz), 6.78-6.86 (m, 2H), 7.02-7.07 (m, 1H), 7.21-7.24 (m, 1H), 7.48 (d, 1H, J=8.8 Hz), 7.68-7.71 (m, 1H)

MS (ESI) m/z 464.3 ([M+H]$^+$)

Example 30

7-(3-(4-(3-(6-fluoro-benzisoxazole)-1-piperidyl)-n-propoxy))-4-hydroxymethyl-2H-benzopyran-2-one (30)

The target compound was synthesized according to Scheme 3.

1) 50 ml of concentrated sulfuric acid was stirred in an ice bath, to which was added 5.5 g of resorcinol and added 8 g of 4-chloro ethyl acetoacetate dropwise. The solution turned yellowish and turbid slowly. The reaction was performed at room temperature overnight. The reaction liquid was poured into ice/water mixture, and a lot of white solid was precipitated, which was filtrated. The cake was washed with water. The cake was recrystallized with 40% ethanol to give 7.5 g of white crystal. Melting point: 183-185° C., yield: 84%.

2) 5 g of the product of step 1) was added to 300 ml of water, and the mixture was heated under reflux for 30 hours. After the reaction was completed, the reaction mixture was filtrated while it was warm. The filtrate was cooled with ice and the needle-shaped solid was precipitated. Standing for 1 hour allowed a lot of solid to precipitate, which was filtrated. The cake was washed with water, dried and recrystallized with 30% ethanol to give 4.1 g of white solid. Melting point: 212-214° C., yield: 91%.

3) 6 g of the product of step 2), 8 g of anhydrous potassium carbonate, 100 ml of acetone and 8 g of 1,3-dibromopropane were heated under reflux for 12 hours and then cooled to room temperature, and filtrated. The solvent was distilled to give yellowish oil, which was passed through a column to give 4.5 g of white solid. Yield: 72.68%.

4) To 0.62 g of the product of step 3) were added 0.6 g of 6-fluoro-3-(4-piperidyl)-1,2-benzisoxazole hydrochloride, 2 g of anhydrous potassium carbonate, 0.2 g of potassium iodide and 25 ml of acetonitrile, and the mixture was heated under reflux for 12 hours, and then cooled to room temperature. The solvent was distilled and the residue was dissolved with dichloromethane, washed with water, dried with anhydrous magnesium sulfate, and filtrated. The solvent was distilled to give yellowish oil, which was passed through a column to give 0.3 g of white solid. Melting point: 144-146° C., yield: 33.7%.

$^1$H NMR (CDCl$_3$) δ 2.05-2.09 (m, 8H), 2.60 (t, 2H, J=14.4 Hz), 3.08-3.11 (m, 3H), 4.11 (t, 2H, J=12.8 Hz), 4.88 (s, 2H), 6.47 (s, 1H), 6.84-6.86 (m, 2H), 7.06-7.07 (m, 1H), 7.23-7.25 (m, 1H), 7.41-7.43 (m, 1H), 7.71-7.72 (m, 1H)

MS (ESI) m/z 453.3 ([M+H]$^+$)

Example 31

7-(4-(4-(3-(6-fluoro-benzisoxazole)-1-piperidyl)-n-butoxy))-4-hydroxymethyl-2H-benzopyran-2-one (31)

The target compound was prepared according to the procedures of Example 30, using 1,4-dibromobutane instead of 1,3-dibromopropane.

Melting point: 160-162° C.

$^1$H NMR (CDCl$_3$) δ 1.73-1.89 (m, 4H), 2.08-2.17 (m, 6H), 2.49 (t, 2H, J=14.4 Hz), 3.08-3.11 (m, 3H), 3.62 (br, 1H), 4.05 (t, 2H, J=12.4 Hz), 4.88 (s, 2H), 6.46 (s, 1H), 6.83-6.85 (m, 2H), 7.03-7.08 (m, 1H), 7.23-7.25 (m, 1H), 7.42 (d, 1H, J=8.8 Hz), 7.68-7.72 (m, 1H)

MS (ESI) m/z 467.3 ([M+H]$^+$)

Example 32

7-(3-(4-(3-(6-fluoro-benzisoxazole)-1-piperidyl)-2-hydroxylpropoxy))-4-methyl-2H-benzopyran-2-one (32)

The target compound was synthesized according to Scheme 4.

3.2 g of 4-methyl-7-hydroxylcoumarin, 20 ml of epoxy chloropropane, 5 ml of 10% potassium hydroxide solution were added to 25 ml of ethanol and the mixture was heated under reflux for 4 hours, and then cooled to room temperature after the reaction was completed. The solvent was distilled and to the residue was added dichloromethane, washed with water and dried with anhydrous magnesium sulfate. The solvent was distilled to give solid, which was recrystallized with anhydrous ethanol to give 3 g of white solid. Yield: 71.8%.

0.84 g of the product of the first step and 0.83 g of 6-fluoro-3-(4-piperidyl)-1,2-benzisoxazole were added to 50 ml of anhydrous methanol and the mixture was heated under reflux for 4 hours. White solid was precipitated. The reaction mixture was cooled to room temperature and filtrated. The cake was washed with cold methanol to give 1.2 g of white solid. Melting point: 183-185° C., yield: 66.8%.

$^1$H NMR (CDCl$_3$) δ 2.08-2.14 (m, 4H), 2.26-2.27 (m, 1H), 2.40 (s, 3H), 2.59-2.65 (m, 3H), 3.02-3.20 (m, 3H), 3.63 (br, 1H), 4.08-4.18 (m, 3H), 6.15 (s, 1H), 6.85 (d, 1H, J=2.8 Hz), 6.91-6.93 (m, 1H), 7.06-7.09 (m, 1H), 7.24-7.27 (m, 1H), 7.51 (d, 1H, J=8.8 Hz), 7.66-7.69 (m, 1H)

MS (ESI) m/z 453.2 ([M+H]$^+$)

Example 33

7-(3-(4-(3-(6-fluoro-benzisoxazole)-1-piperidyl)-2-hydroxylpropoxy))-4-phenyl-2H-benzopyran-2-one (33)

The target compound was prepared according to the procedures of Example 32, using 4-phenyl-7-hydroxylcoumarin instead of 4-methyl-7-hydroxylcoumarin.

Melting point: 193-195° C.

$^1$H NMR (CDCl$_3$) δ 2.08-2.14 (m, 4H), 2.24-2.27 (m, 1H), 2.52-2.68 (m, 3H), 3.02-3.21 (m, 3H), 3.63 (br, s, 1H), 4.09 (t, 2H, J=9.6 Hz), 4.17-4.18 (m, 1H), 6.23 (s, 1H), 6.84-6.87 (m, 1H), 6.93-6.94 (m, 1H), 7.05-7.10 (m, 1H), 7.24-7.27 (m, 1H), 7.39-7.51 (m, 6H), 7.66-7.69 (m, 1H)

MS (ESI) m/z 515.3 ([M+H]$^+$)

Example 34

7-(4-(4-(3-(6-fluoro-benzisoxazole)-1-piperidyl)-n-propoxy))-4-phenyl-benzopyran-2-one (34)

The target compound was synthesized according to Scheme 5.

1) To 5.5 g of resorcinol, 7.4 g of cinnamic acid were added 200 ml of concentrated hydrochloric acid, to which was introduced hydrochloride gas. The mixture was heated under reflux for 6 hours and then cooled to room temperature. The solid was precipitated and filtrated. The cake was washed with water, dried under vacuum, recrystallized with toluene to give 8.1 g of white solid. Melting point: 104-106° C., yield: 67.5%.

2) 3.1 g of the product of step 1), 6 g of anhydrous potassium carbonate, 50 ml of acetone, 6 g of 1,4-dibromobutane were heated under reflux, being monitored with TLC. The reaction was completed after about 6 hours, and then the reaction mixture was cooled to room temperature, and filtrated. The solvent was removed by rotation to give yellowish oil, which was passed through a column to give 2.9 g of colorless oil. Yield: 60.4%.

3) To 1.8 g of product of step 2) were added 1.26 g of 6-fluoro-3-(4-piperidyl)-1,2-benzisoxazole hydrochloride, 2.6 g of anhydrous potassium carbonate, 0.3 g of potassium iodide and 30 ml of acetonitrile, and the mixture was heated under reflux for 12 hours. The reaction mixture was cooled to room temperature after the reaction was completed. The solvent was removed by rotation and a suitable amount of dichloromethane was added. The mixture was washed with water, and dried with anhydrous magnesium sulfate. The solvent was distilled to give yellowish oil, which was passed through a column to give 1.6 g of colorless oil. Yield: 65.0%.

$^1$H NMR (CDCl$_3$) δ 1.61-1.76 (m, 5H), 2.07-2.16 (m, 6H), 2.47 (t, 2H, J=14.8 Hz), 3.08-3.10 (m, 5H), 3.89 (t, 2H, J=12.4 Hz), 6.38-6.40 (m, 2H), 7.01-7.05 (m, 2H), 7.22-7.27 (m, 6H), 7.65-7.70 (m, 1H)

MS (ESI) m/z 515.3 ([M+H]$^+$)

TABLE 1

Numbering of the preferable compounds prepared in the Examples and the structures

| No. | Compound Structure |
|---|---|
| 1 | [Structure: coumarin-O-(CH$_2$)$_4$-N(piperidine)-6-fluoro-benzisoxazole] |
| 2 | [Structure: coumarin-O-(CH$_2$)$_4$-N(piperazine)-benzisothiazole] |

TABLE 1-continued

Numbering of the preferable compounds prepared in the Examples and the structures

| No. | Compound Structure |
|---|---|
| 3 | 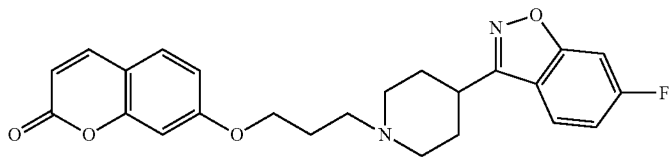 [SMILES: O=c1ccc2ccc(OCCCN3CCC(c4noc5cc(F)ccc45)CC3)cc2o1] |
| 4 | 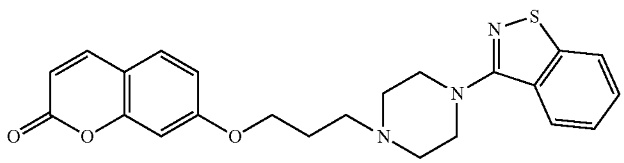 [SMILES: O=c1ccc2ccc(OCCCN3CCN(c4nsc5ccccc45)CC3)cc2o1] |
| 5 | 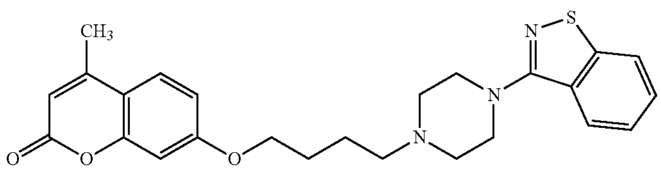 [SMILES: Cc1cc(=O)oc2cc(OCCCCN3CCN(c4nsc5ccccc45)CC3)ccc12] |
| 6 | 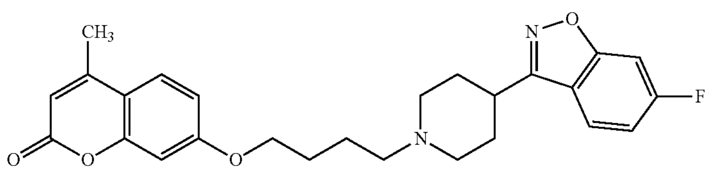 [SMILES: Cc1cc(=O)oc2cc(OCCCCN3CCC(c4noc5cc(F)ccc45)CC3)ccc12] |
| 7 | 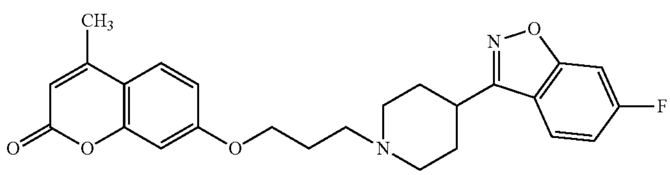 [SMILES: Cc1cc(=O)oc2cc(OCCCN3CCC(c4noc5cc(F)ccc45)CC3)ccc12] |
| 8 | 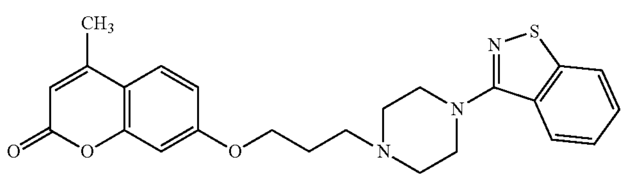 [SMILES: Cc1cc(=O)oc2cc(OCCCN3CCN(c4nsc5ccccc45)CC3)ccc12] |
| 9 | 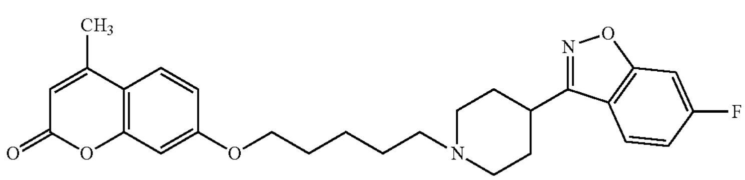 [SMILES: Cc1cc(=O)oc2cc(OCCCCCN3CCC(c4noc5cc(F)ccc45)CC3)ccc12] |
| 10 | 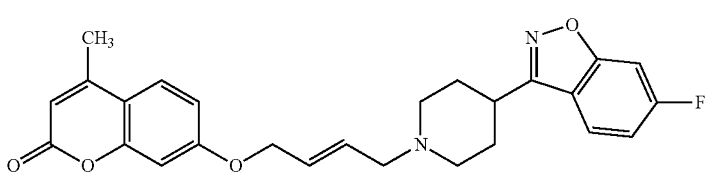 [SMILES: Cc1cc(=O)oc2cc(OC/C=C/CN3CCC(c4noc5cc(F)ccc45)CC3)ccc12] |

TABLE 1-continued
Numbering of the preferable compounds prepared in the Examples and the structures
| No. | Compound Structure |
|---|---|
| 11 | 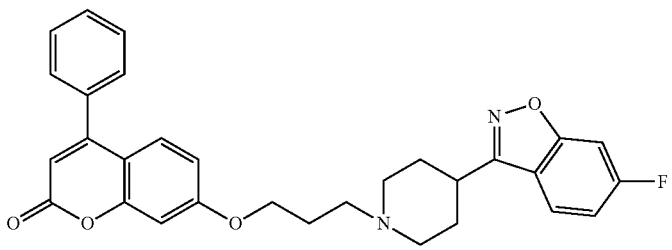 [SMILES: O=c1cc(-c2ccccc2)c2ccc(OCCCN3CCC(c4noc5cc(F)ccc45)CC3)cc2o1] |
| 12 | 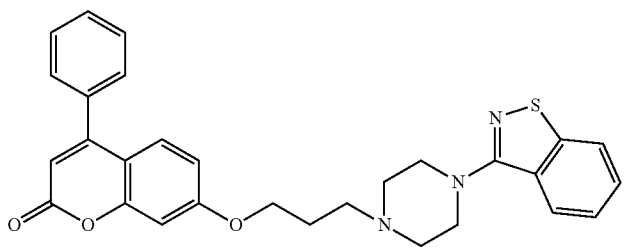 [SMILES: O=c1cc(-c2ccccc2)c2ccc(OCCCN3CCN(c4nsc5ccccc45)CC3)cc2o1] |
| 13 | 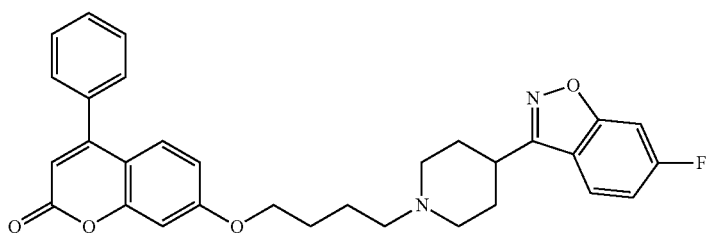 [SMILES: O=c1cc(-c2ccccc2)c2ccc(OCCCCN3CCC(c4noc5cc(F)ccc45)CC3)cc2o1] |
| 14 | 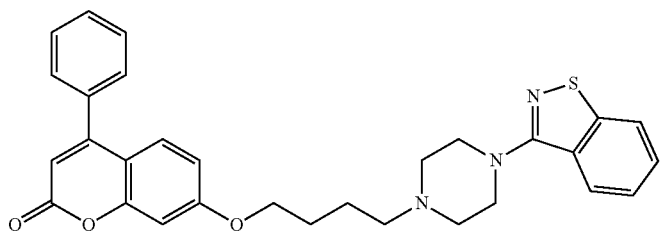 [SMILES: O=c1cc(-c2ccccc2)c2ccc(OCCCCN3CCN(c4nsc5ccccc45)CC3)cc2o1] |
| 15 | 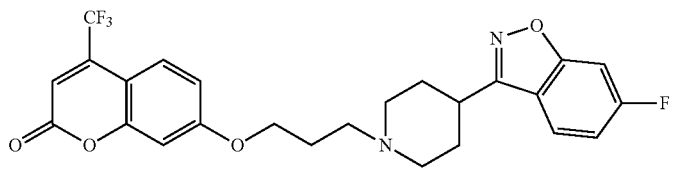 [SMILES: O=c1cc(C(F)(F)F)c2ccc(OCCCN3CCC(c4noc5cc(F)ccc45)CC3)cc2o1] |
| 16 | 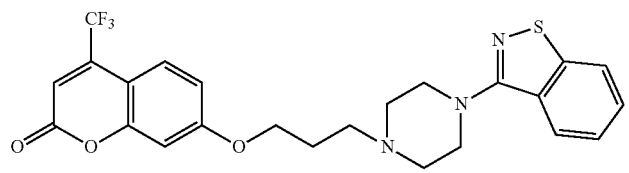 [SMILES: O=c1cc(C(F)(F)F)c2ccc(OCCCN3CCN(c4nsc5ccccc45)CC3)cc2o1] |
| 17 | 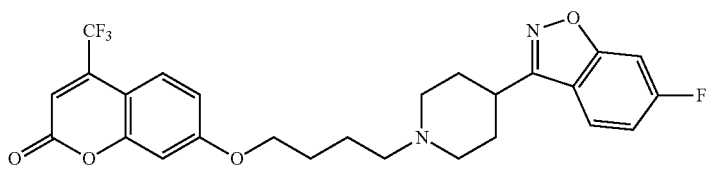 [SMILES: O=c1cc(C(F)(F)F)c2ccc(OCCCCN3CCC(c4noc5cc(F)ccc45)CC3)cc2o1] |

TABLE 1-continued

Numbering of the preferable compounds prepared in the Examples and the structures

| No. | Compound Structure |
|---|---|
| 18 | 4-(trifluoromethyl)-7-(4-(4-(benzo[d]isothiazol-3-yl)piperazin-1-yl)butoxy)-2H-chromen-2-one |
| 19 | 8-chloro-7-(4-(4-(6-fluorobenzo[d]isoxazol-3-yl)piperidin-1-yl)butoxy)-4-methyl-2H-chromen-2-one |
| 20 | 7-(4-(4-(benzo[d]isothiazol-3-yl)piperazin-1-yl)butoxy)-8-chloro-4-methyl-2H-chromen-2-one |
| 21 | 8-chloro-7-(3-(4-(6-fluorobenzo[d]isoxazol-3-yl)piperidin-1-yl)propoxy)-4-methyl-2H-chromen-2-one |
| 22 | 7-(3-(4-(benzo[d]isothiazol-3-yl)piperazin-1-yl)propoxy)-8-chloro-4-methyl-2H-chromen-2-one |
| 23 | 7-(4-(4-(6-fluorobenzo[d]isoxazol-3-yl)piperidin-1-yl)butoxy)-4,8-dimethyl-2H-chromen-2-one |
| 24 | 7-(4-(4-(benzo[d]isothiazol-3-yl)piperazin-1-yl)butoxy)-4,8-dimethyl-2H-chromen-2-one |

TABLE 1-continued
Numbering of the preferable compounds prepared in the Examples and the structures
| No. | Compound Structure |
|---|---|
| 25 | 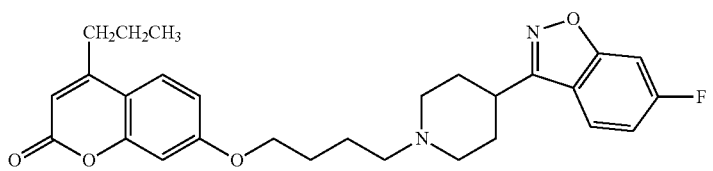 |
| 26 | 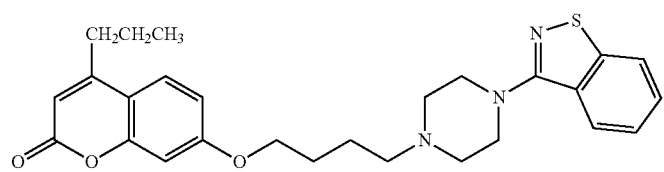 |
| 27 | 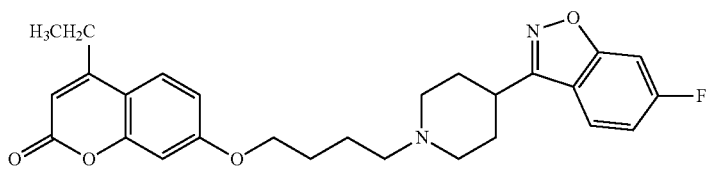 |
| 28 | 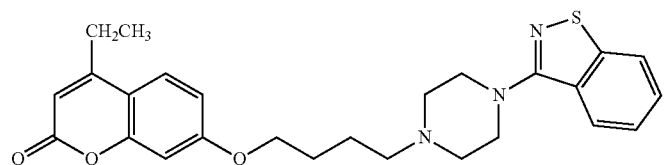 [SMILES: CCc1cc(=O)oc2cc(OCCCCN3CCN(c4nsc5ccccc45)CC3)ccc12] |
| 29 | 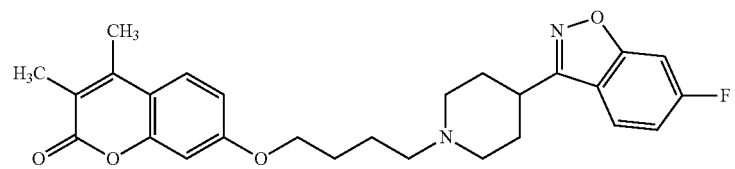 [SMILES: Cc1c(C)c2ccc(OCCCCN3CCC(c4noc5cc(F)ccc45)CC3)cc2oc1=O] |
| 30 | 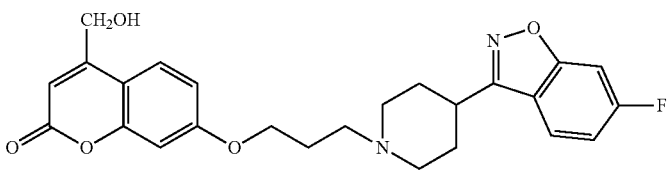 [SMILES: O=c1cc(CO)c2ccc(OCCCN3CCC(c4noc5cc(F)ccc45)CC3)cc2o1] |
| 31 | 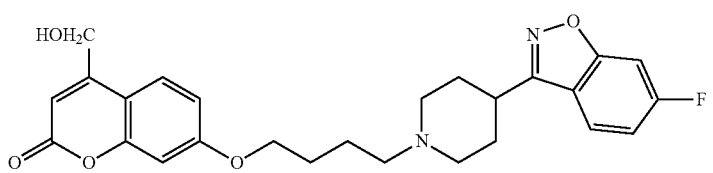 [SMILES: O=c1cc(CO)c2ccc(OCCCCN3CCC(c4noc5cc(F)ccc45)CC3)cc2o1] |

TABLE 1-continued

Numbering of the preferable compounds prepared in the Examples and the structures

| No. | Compound Structure |
|---|---|
| 32 | (structure: 4-methyl coumarin with 7-O-CH₂-CH(OH)-CH₂-N-piperidine-(6-fluoro-benzisoxazol-3-yl)) |
| 33 | (structure: 4-phenyl coumarin with 7-O-CH₂-CH(OH)-CH₂-N-piperidine-(6-fluoro-benzisoxazol-3-yl)) |
| 34 | (structure: 4-phenyl-3,4-dihydrocoumarin with 7-O-(CH₂)₄-N-piperidine-(6-fluoro-benzisoxazol-3-yl)) |

B. Pharmacological Examples

Example 35

Preparation of 5HT$_{1A}$ Membrane

Rats were sacrificed by cervical dislocation on ice. Brain striatum was rapidly taken, and 2 brain striatums were combined into a centrifuge tube, to which 3 ml of buffer (0.05 M Tris-HCl buffer, containing 0.1% ascorbic acid, 10 μm pargyline and 4 mM CaCl$_2$) was added. Homogenization was conducted for 3-4 s at level 4 for four times, and then 5 ml of buffer was added (0.05 M Tris-HCl buffer, containing 0.1% ascorbic acid, 10 μm pargyline and 4 mM CaCl$_2$). Incubation at 37° C. was conducted for 10 min, the weight of the tubes were adjusted using a balance after incubation. Centrifugation was conducted at 12000 r, 4° C. for 20 min, the supernatant was discarded, and 3 ml of buffer was added (0.05 M Tris-HCl buffer, containing 0.1% ascorbic acid, 10 μm pargyline and 4 mM CaCl$_2$). Vortex mixer was used for blending, and then 5 ml of buffer was added (0.05 M Tris-HCl buffer, containing 0.1% ascorbic acid, 10 μm pargyline and 4 mM CaCl$_2$). Centrifugation was conducted and repeated 3 times. After the centrifugations, the supernatant was discarded, and the pellets were stored at −80° C. for future use.

Materials for the Receptor Binding Assay

Isotope ligand $^3$H-8-OH-DPAT (67.0 Ci/mmol) was purchased from PerkinElmer Company; 5-HT was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with appropriate amount of homogenized liquid, and homogenizer was used for evenly dispersing. 15 tubes were mixed into a 100 ml container, and appropriate amount of homogenized liquid was added to give 50 ml of membrane suspension, which was reserved for future use.

(2) 100 μL of membrane preparation and 100 μL of homogenized liquid were added into each reaction tube.

(3) 100 μL of homogenized liquid was added into the total binding tube (TB), 100 μL of 5-HT (final concentration $10^{-5}$ M) was added into the non-specific binding tube (NB), and 100 μL of the test compound (final concentration $10^{-5}$ M) was added into the specific binding tube (SB) for each compound.

(4) 10 μL of radioactive ligand $^3$H-8-OH-DPAT was respectively added into each reaction tube (2 parallel tubes were used for each reaction tube, and each of them was placed on ice when adding sample).

(5) Each reaction tube was incubated at 37° C. for 10 min; after the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate(1%)=(Total binding tube cpm−compound cpm)/(Total binding tube cpm−non-specific binding tube cpm)×100%

Each assay for the compounds was conducted in duplicate. The results are listed in Table 2.

Example 36

Preparation of 5HT$_{2A}$ Membrane

Rats were sacrificed by cervical dislocation on ice. Brain striatum was rapidly taken, and 2 brain striatums were combined into a centrifuge tube, to which 3 ml of buffer (0.05 M Tris-HCl buffer: 6.05 g of Tris was dissolved in 1000 ml of double-distilled water, and concentrated HCl was used to adjust to pH 7.5) was added, homogenization was conducted for 3-4 s at level 4 for four times, and then 5 ml of buffer was added. Incubation at 37° C. was conducted for 10 min, the weight of the tubes were adjusted using a balance after incubation. Centrifugation was conducted at 12000 r, 4° C. for 20 min, the supernatant was discarded, and 3 ml of buffer was added (0.05 M Tris-HCl buffer: 6.05 g of Tris was dissolved in 1000 ml of double-distilled water, and concentrated HCl was used to adjust to pH 7.5). Vortex mixer was used for blending, and then 5 ml of buffer was added. Centrifugation was conducted (repeated 3 times). After the centrifugations, the supernatant was discarded, and the pellets were stored at −80° C. for future use.

Materials for the Receptor Binding Assay

Isotope ligand [$^3$H]-Ketanserin (67.0 Ci/mmol) was purchased from PerkinElmer Company; Methysergide was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with homogenized liquid, and homogenizer was used for evenly dispersing. 15 tubes were mixed into a 100 ml container, and appropriate amount of homogenized liquid was added to give 50 ml of membrane suspension, which was reserved for future use.

(2) 100 μL of membrane preparation and 100 μL of buffer were added into each reaction tube.

(3) 100 μL of homogenized liquid was added into the total binding tube (TB), 100 μL of Methysergide (final concentration $10^{-5}$ M) was added into the non-specific binding tube (NB), and 100 μL of the test compound (final concentration $10^{-5}$ M) was added into the specific binding tube (SB) for each compound.

(4) 10 μL of radioactive ligand $^3$H-Ketanserin was respectively added into each reaction tube (2 parallel tubes were used for each reaction tube, and each of them was placed on ice when adding sample).

(5) Each of the reaction tubes was incubated at 37° C. for 15 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate(1%)=(Total binding tube cpm−compound cpm)/(Total binding tube cpm−non-specific binding tube cpm)×100%

Each assay for the compounds was conducted in duplicate. The results are listed in Table 2.

Example 37

Preparation of D$_2$ Membrane

Rats were sacrificed by cervical dislocation on ice. Brain striatum was rapidly taken, and 2 brain striatums were combined into a centrifuge tube, to which 3 ml of buffer (0.05 M Tris-HCl buffer, containing NaCl 120 mM, KCl 5 mM, MgCl$_2$ 1 mM, CaCl$_2$ 1 mM) was added, homogenization was conducted for 3-4 s at level 4 for four times, and then 5 ml of buffer was then added. The weight of the homogenized tubes were adjusted using a balance, and centrifugation was conducted at 12000 r, 4° C. for 20 min. The supernatant was discarded, and 3 ml of buffer was added (0.05 M Tris-HCl buffer, containing NaCl 120 mM, KCl 5 mM, MgCl$_2$ 1 mM, CaCl$_2$ 1 mM). Vortex mixer was used for blending, and then 5 ml of buffer was added (0.05 M Tris-HCl buffer, containing NaCl 120 mM, KCl 5 mM, MgCl$_2$ 1 mM, CaCl$_2$ 1 mM). Centrifugation was conducted (repeated 3 times). After the centrifugations, the supernatant was discarded, and the pellets were stored at −80° C. for future use.

Materials for the Receptor Binding Assay

Isotope ligand $^3$H-Spiperone (67.0 Ci/mmol) was purchased from PerkinElmer Company; Butaclamol was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with appropriate amount of homogenized liquid, and homogenizer was used for evenly dispersing. 15 tubes were mixed into a 100 ml container, and appropriate amount of homogenized liquid was added to give 50 ml of membrane suspension, which was reserved for future use.

(2) 100 μL of membrane preparation and 100 μL of buffer were added into each reaction tube.

(3) 100 μL of homogenized liquid was added into the total binding tube (TB), 100 μL of Butaclamol (final concentration $10^{-5}$ M) was added into the non-specific binding tube (NB), and 100 μL of the test compound (final concentration $10^{-5}$ M) was added into the specific binding tube (SB) for each compound.

(4) 10 μL of radioactive ligand $^3$H-Spiperone was respectively added into each reaction tube (2 parallel tubes were used for each reaction tube, and each of them was placed on ice when adding sample).

(5) Each of the reaction tubes was incubated at 37° C. for 20 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibitory rate(1%)=(Total binding tube cpm−compound cpm)/(Total binding tube cpm−non-specific binding tube cpm)×100%

Each assay for the compounds was conducted in duplicate. The results are listed in Table 2.

Example 38

$D_3$ Receptor Assay

Cells

In HEK-293 cells, after 48-72 hours, receptor proteins were expressed on membrane in large amount. After the cells were centrifuged at 1000 rpm for 5 min, the supernatant was discarded, and the cell pellet was collected and stored in a −20° C. fridge for reservation. It was re-suspended with Tris-Cl (pH 7.4) in the assay.

Materials for the Assay $D_3$ receptor isotope ligand [3H]-Spiperone was purchased from Amersham Company; (+)Butaclamol was purchased from RBI Company; GF/C glass fiber filter paper was purchased from Whatman Company; lipid-soluble scintillation solution. Tris was divided into aliquots by Genetimes Technology Inc.

Procedures

Competitive binding test for receptors: 20 μl of each of the test compounds and 20 μl of the radioactive ligand together with 160 μl of the receptor proteins were added into the reaction tubes, and the final concentrations of the test compound and the positive drug were all 10 μmol/L. After 50 min of incubation in 30° C. water bath, the tubes were immediately moved to ice bath to terminate the reactions. GF/C glass fiber filter papers were used for rapid sucking filtration on a Millipore cell sample collector, elution buffer (50 mM Tris-HCl, PH 7.4) was applied for 3 ml×3 times, and microwave was applied for 4-5 min for drying. The filter papers were moved into 0.5 ml centrifuge tubes, and 500 μl of lipid-soluble scintillation solution was added. The tubes were allowed to stand still for over 30 min in dark, and the intensities of radioactivity were measured by a counter. The percentage inhibition rates of each compound against the binding of isotope ligands were calculated according to the following formula:

Inhibition rate(1%)=(Total binding tube cpm−compound cpm)/(Total binding tube cpm−non-specific binding tube cpm)×100%

The results are listed in Table 2.

Example 39

Preparation of $5HT_{2C}$ Membrane

Rats were sacrificed by cervical dislocation on ice. Brain striatum was rapidly taken, and 2 brain striatums were combined into a centrifuge tube, to which 3 ml of buffer (0.05 M Tris-HCl buffer: 6.05 g of Tris was dissolved in 1000 ml of double-distilled water, and concentrated HCl was used to adjust to pH 7.5) was added, homogenization was conducted for 3-4 s at level 4 for four times, and then 5 ml of buffer was added. Incubation at 37° C. was conducted for 10 min, the weight of the tubes were adjusted using a balance after the incubation. Centrifugation was conducted at 12000 r, 4° C. for 20 min, the supernatant was discarded, and 3 ml of buffer was added (0.05 M Tris-HCl buffer: 6.05 g of Tris was dissolved in 1000 ml of double-distilled water, and concentrated HCl was used to adjust to pH 7.5). Vortex mixer was used for blending, and then 5 ml of buffer was added. Centrifugation was conducted (repeated 3 times). After the centrifugations, the supernatant was discarded, and the pellets were stored at −80° C. for future use.

Materials for the Receptor Binding Assay

Isotope ligand [$^3$H]-mesulergine (67.0 Ci/mmol) was purchased from PerkinElmer Company; mianserin was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with appropriate amount of homogenized liquid, and homogenizer was used for evenly dispersing. 15 tubes were mixed into a 100 ml container, and appropriate amount of homogenized liquid was added to give 50 ml of membrane suspension, which was reserved for future use.

(2) 100 μL of membrane preparation and 100 μL of buffer were added into each reaction tube.

(3) 100 μL of homogenized liquid was added into the total binding tube (TB), 100 μL of mianserin (final concentration $10^{-5}$ M) was added into the non-specific binding tube (NB), and 100 μL of the test compound (final concentration $10^{-5}$ M) was added into the specific binding tube (SB) for each compound.

(4) 10 μL of radioactive ligand [$^3$H]-mesulergine was respectively added into each reaction tube (2 parallel tubes were used for each reaction tube, and each of them was placed on ice when adding sample).

(5) Each of the reaction tubes was incubated at 37° C. for 15 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate(1%)=(Total binding tube cpm−compound cpm)/(Total binding tube cpm−non-specific binding tube cpm)×100%

Each assay for the compounds was conducted in duplicate. The results are listed in Table 2.

The results of in vitro assay indicated that, compounds 1, 6, 7, 12, 18 and 22 have relatively stronger affinities for four receptors ($D_2$, $D_3$, $5\text{-}HT_{1A}$ and $5\text{-}HT_{2A}$) while lower affinities for $5\text{-}HT_{2C}$.

Example 40

MK-801 Induced High Activity—the In Vivo Anti-Schizophrenia Activity of the Compounds Animals and Reagents Healthy mice of Kunming breed (with half male and half female, (20±2)g) were provided by Qinglongshan Animal Cultivation Center, Nanjing.

Ascorbic acid was provided by Sinopharm Chemical Reagent Co. Ltd.

MK-801 was produced by Sigma Company, USA; the formulation method: 0.1% vitamin C was used to formulate a 1 mg/ml solution.

Test positive drugs: haloperidol, clozapine, risperidone, olanzapine, aripiprazole, ziprasidone, quetiapine.

Tween 80, with the concentration of 10%.

Procedures

Mice with qualified body weight were selected, and randomly divided into blank group, model group, positive control group (risperidone group) and drug group. 10% Tween was administered intragastrically to the blank group and the model group at 0.1 ml/10 g; risperidone was administered intragastrically to the positive control group at 0.1 mg/kg; and corresponding amounts of drugs were administered intragastrically to the drug groups, respectively. 1 h after the administration, 0.1% of ascorbic acid was intraperitoneally injected to the blank group at 0.1 ml/10 g; and the model group, the positive control group (30 min) and the drug group were intraperitoneally injected the MK-801 solution at 0.1 mg/kg. Subsequently, the spontaneous activities of the mice of each group in 90 min were measured. The results are listed in Table 3.

The results of this assay indicate that, when compared to the model group, risperidone, compound 19 and 23 can not only significantly improve the MK-801 induced high activity, but also effectively improve the apomorphine induced clambering symptoms, and they did not cause EPS at effective dosage, indicating that they have notable anti-schizophrenia effects.

Example 41

Apomorphine Induced Clambering Assay of Mice

Animals

Healthy KM mice (male, with body weight of 18-22 g) were provided by Qinglongshan Animal Cultivation Center, Nanjing.

Main Reagents

Test positive drugs: haloperidol, clozapine, risperidone, olanzapine, aripiprazole, ziprasidone, quetiapine.

Apomorphine provided by Sigma Company was dissolved in 0.9% NaCl (containing 0.1% vitamin C) before use, and was freshly formulated before use.

Vitamin C, F20061113, was provided by Sinopharm Chemical Reagent Co. Ltd.

Sodium chloride injection, H32026305, was provided by Xuzhou No. 5 Pharmaceutical Factory Co. Ltd.

Instruments: self-made clambering cage, chronograph.

Procedures: apomorphine induced clambering assay of mice

KM mice (male, with body weight of 18-22 g) were randomly divided into negative control group, model group, positive drug groups for each dosage (risperidone, aripiprazole, ziprasidone, quetiapine, olanzapine, haloperidol, clozapine), and compound groups for each dosage (the specific dosages are listed in the following Table), with 10 mice in each group. Corresponding solvent double-distilled water was administered intragastrically to the negative control group and the model group, corresponding positive drugs were administered intragastrically to the positive drug groups (a small amount of acetic acid was first added and then double-distilled water was added when dissolving), and corresponding dosages of compounds were administered intragastrically to the compound groups for each dosage, with the volume for intragastric administration as 0.1 ml/10 g. 1 hour after the intragastric administration, apomorphine was subcutaneously injected (1 mg/kg), with the volume as 0.1 ml/10 g. After the injection of apomorphine, the mice were immediately put into the clambering cages. After 5 min of adaptation, the behaviors of the mice at 10-11, 20-21, and 30-31 min after the injection of apomorphine were observed and scored. Scoring criteria: 4 paws on the floor was scored as 0; 2 forepaws on the cage was scored as 1; and 4 paws on the cage was scored as 2.

Example 42

Catalepsy Assay

Animals

Healthy mice of Kunming breed (with half male and half female, (22±2)g) were provided by Qinglongshan Animal Cultivation Center, Nanjing.

Main reagents: the test drugs, haloperidol, clozapine, risperidone, olanzapine, aripiprazole, ziprasidone.

Instruments: self-made bar-grabbing apparatus: stainless steel bar in mice box, which was 0.3 cm in diameter and 5 cm above the bench.

Procedures

KM mice (half male and half female, with body weight of 20-24 g) were randomly divided into negative control group, model group, positive drug groups for each dosage (risperidone, aripiprazole, ziprasidone, quetiapine, olanzapine, haloperidol, clozapine), and compound groups for each dosage, with 10 mice in each group. Corresponding solvent double-distilled water was administered intragastrically to the negative control group and the model group, corresponding positive drugs were administered intragastrically to the positive drug groups (a small amount of acetic acid was first added and then double-distilled water was added when dissolving), and corresponding dosages of compounds were administered intragastrically to the compound groups for each dosage, with the volume for intragastric administration as 0.1 ml/10 g. At 30 min, 60 min, 90 min after the intragastric administration, the two forepaws of the mice were gently placed on the bars (which were 20 cm in length, 0.3 cm in diameter, and 5.5 cm above the bench), and the hindpaws of the animals were placed on the bottom of the box. The durations for the mice to maintain the posture with the two forepaws on the bars were recorded, and 30 s of spasticity without moving was considered as the positive response. In the case the forepaws of the mice were not put down persistently, the observation was terminated at 60 s. The numbers of animals with positive response in each of the compound dosage groups were counted.

Example 43

Acute Toxicity Study

Limit Test of Sequential Assay

KM mice (half male and half female) were randomly divided into several groups (with 2-5 mice in each group), which were respectively the 2000 mg/kg groups for each compound, and the solvent group. 0.2 ml/10 g were administered intragastrically. The death of the animals in 3 days were observed. (In the case 3 or more animals survived in 3 days without notable abnormity in their life states, the observation was continued until the assay was completed in 7 days. In the case 3 or more animals died in 3 days, the median lethal dose method was used to determine the $LD_{50}$).

Pre-Assay for the Median Lethal Dose Method

KM mice (half male and half female) were randomly divided into several groups (with 4 mice in each group), which were respectively the 1500 mg/kg, 1000 mg/kg, 500 mg/kg groups for each compound, and the solvent group. 0.2 ml/10 g were administered intragastrically, and the death of the animals in 1-3 days were observed.

Results

The $LD_{50}$ of single intragastric administration in mice was greater than 2000 mg/kg, which was comparable to aripiprazole (93 mg/kg) and ziprasidone (>2000 mg/kg), and was far greater than risperidone (82.1 mg/kg), indicating a relatively low acute toxicity.

TABLE 2

The inhibition or $IC_{50}$ of the compounds for each receptor

| Compound No. | $D_2$ inhibition % | $5HT_{1A}$ inhibition % or ($IC_{50}$, nM) | $5HT_{2A}$ inhibition % or (IC50, nM) | $D_3$ inhibition % | $5HT_{2C}$ inhibition % |
|---|---|---|---|---|---|
| 1 | 128.3% | 9.61 [a] | 1.53 [a] | 97.6% | 88.0% |
| 2 | 80.6% | 99.4% | 103.4% | — | — |
| 3 | 106.3% | 42.3% | 101.2% | — | — |
| 4 | 49.2% | 101.2% | 59.1% | — | — |
| 5 | 88.5% | 113.5% | 104.4% | — | — |
| 6 | 101.3% | 3.52 [a] | 0.39 [a] | 100.4% | 91.4% |
| 7 | 102.8% | 5.95 [a] | 0.69 [a] | 101.1% | 82.0% |
| 8 | 73.8% | 98.5% | 88.6% | — | — |
| 9 | 102.4% | 88.8% | 119.6% | — | — |
| 10 | 111.2% | 101.5% | 109.1% | — | — |
| 11 | 18.5% | 35.3% | 57.8% | — | — |
| 12 | 124.1% | 127.3 [a] | 9.26 [a] | 103.1% | 93.4% |
| 13 | 65.2% | 111.4% | 67.2% | — | — |
| 14 | 68.6% | 95.5% | 83.4% | — | — |
| 15 | 94.6% | 107.4% | 83.3% | — | — |
| 16 | 114.6% | 104.1% | 96.3% | — | — |
| 17 | 92.3% | 101.4% | 95.9% | — | — |
| 18 | 113.3% | 6.19 [a] | 0.79 [a] | 103.3% | 77.6% |
| 19 | 27.8% | 103.7% | 119.2% | — | — |
| 20 | 9.7% | 92.8% | 15.5% | — | — |
| 21 | 32.9% | 100.8% | 90.1% | — | — |
| 22 | 111.8% | 12.81 [a] | 6.88 [a] | 103.8% | 99.8% |
| 23 | 6.9% | 78.5% | 78.6% | — | — |
| 24 | 98.1% | 105.0% | 97.4% | — | — |
| 25 | 70.7% | 84.5% | 40.2% | — | — |
| 26 | 61.9% | 99.7% | 128.9% | — | — |
| 27 | 84.0% | 65.7% | 123.6% | — | — |
| 28 | 58.8% | 11% | 56.1% | — | — |
| 29 | 43.2% | 97.1% | 24.7% | — | — |
| 30 | 20.3% | 82.8% | 98.5% | — | — |
| 31 | 2.4% | 63.9% | 1.8% | — | — |
| 32 | 62.6% | 103.3% | 157.1% | — | — |
| 33 | 110.5% | 23.5% | 128.6% | — | — |
| 34 | 119.6% | 5.9% | 115.4% | — | — |
| aripiprazole | 94.9% | 3.35 [a] | 11.51 [a] | 99.50% | 99.8% |

Note:
("[a]" indicates that the data in the cell is $IC_{50}$ value)

TABLE 3

Results of the in vivo animal model assay of the preferable compounds

| Compoud No. | $LD_{50}$ (po, mg/kg) | MK-801 induced high activity ($ED_{50}$, po, mg/kg) | apomorphine induced clambering ($ED_{50}$, po, mg/kg) | catalepsy ($ED_{50}$, po, mg/kg) | catalepsy/ MK-801 induced high activity | catalepsy/ apomorphine induced clambering |
|---|---|---|---|---|---|---|
| 1 | >2000 | 0.61 | 0.32 | 1.41 | 2.35 | 4.41 |
| 6 | >2000 | 0.32 | 0.11 | 0.68 | 2.13 | 6.18 |
| 7 | 1000-2000 | 0.27 | 0.15 | 1.50 | 5.56 | 10.00 |
| 19 | >2000 | 1.33 | 1.68 | 70.85 | 53.27 | 42.17 |
| 23 | >2000 | 4.24 | 0.21 | 46.14 | 10.88 | 219.71 |
| haloperidol | 20 | 7.42 | 0.10 | 0.44 | 4.40 | 4.89 |
| clozapine | 150 | 2.28 | 17.92 | >50 | >21.93 | >5.58 |
| risperidone | 82.1 | 0.01 | 0.015 | 0.92 | 92.00 | 61.33 |
| olanzapine | 177 | 0.10 | 0.11 | 2.23 | 22.30 | 20.27 |
| aripiprazole | 93 | 0.12 | 0.66 | 2.40 | 20.00 | 11.43 |
| ziprasidone | >2000 | 0.56 | 0.37 | 30.40 | 54.29 | 82.16 |
| quetiapine | 800 | 10.1 | 2.02 | 800.00 | 79.21 | 396.04 |

C. Composition Example

Example 44

Tablet

| Active Ingredient (the compound according to the invention) | 100 mg |
|---|---|
| microcrystalline cellulose | 50 mg |
| lactose | 100 mg |
| Povidone K30 | 9 mg |
| carboxymethyl starch sodium | 12 mg |
| silica | 2.5 mg |
| magnesium stearate | 1.5 mg |

The raw excipients were sieved with 80 mesh for use. The prescription doses of active ingredient, microcrystalline cellulose, lactose, Povidone K30 were weighed and introduced into a high speed mixing granulator, whereby they were mixed uniformly at low speed. A suitable amount of purified water was added, the stiffing was performed at low speed, and high speed shear granulation was carried out. The wet granules were dried at 60° C. for 3 hours, and sieved with 24 mesh. The prescription doses of carboxymethyl starch sodium, silica and magnesium stearate were added for mixing totally. The compression was performed in a rotary tablet press.

Example 45

Capsule (230 mg)

| Active Ingredient (the compound according to the invention) | 100 mg |
|---|---|
| lactose | 80 mg |
| starch | 40 mg |
| Povidone K30 | 7 mg |
| silica | 2 mg |
| magnesium stearate | 1 mg |

The raw excipients were sieved with 80 mesh for use. The prescription doses of active ingredient, lactose, starch, Povidone K30 were weighed and introduced into a high speed mixing granulator, whereby they were mixed uniformly at low speed. A suitable amount of purified water was added, the stirring was performed at low speed, and high speed shear granulation was carried out. The wet granules were dried at 60° C. for 3 hours, and sieved with 24 mesh. The prescription doses of silica and magnesium stearate were added for mixing totally. The capsules were filled in a capsule filling machine.

The invention claimed is:

1. A benzopyrone derivative having the structure of formula (I) or a pharmaceutically acceptable salt thereof,

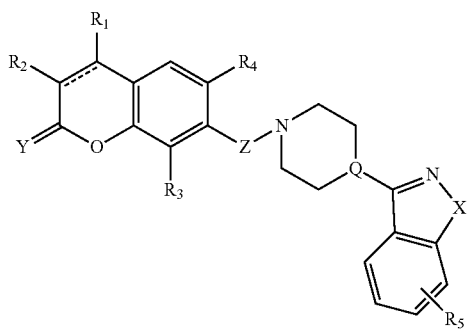

I wherein,

Z is —O(CH$_2$)$_n$, which is unsubstituted or substituted by one or more substituents independently selected from the group consisting of hydroxyl and C$_{1-5}$alkyl, wherein n is an integer of 2-6, and the carbon chain of Z optionally has a double bond(s);

Y is O or S;

Q is N or CH;

X is O, S or NH;

the dashed line represents a single bond or a double bond;

R$_1$, R$_3$, R$_4$ and R$_5$ are each independently H; halogen; cyano; hydroxyl; aryl, which is unsubstituted or substituted by one or more substituents independently selected from the group consisting of halogen, amino and hydroxyl; C$_{1-5}$alkyl, which is unsubstituted or substituted by one or more substituents independently selected from the group consisting of halogen, amino and hydroxyl; or C$_{1-5}$alkoxy, which is unsubstituted or substituted by one or more substituents independently selected from the group consisting of halogen, amino and hydroxyl;

R$_2$ is H; or C$_{1-5}$alkyl, which is unsubstituted or substituted by one or more substituents independently selected from the group consisting of halogen, amino and hydroxyl.

2. The benzopyrone derivative according to claim 1 or the pharmaceutically acceptable salt thereof, wherein Z is —O(CH$_2$)$_n$, which is unsubstituted or substituted by one or more hydroxyl; n is an integer of 2-5; and the carbon chain of Z optionally has a double bond(s).

3. The benzopyrone derivative according to claim 1 or the pharmaceutically acceptable salt thereof, wherein Y is O; X is O or S.

4. The benzopyrone derivative according to claim 1 or the pharmaceutically acceptable salt thereof, wherein R$_1$ is H, phenyl, halophenyl, C$_{1-5}$alkyl, C$_{1-5}$haloalkyl or C$_{1-5}$hydroxylalkyl.

5. The benzopyrone derivative according to claim 4 or the pharmaceutically acceptable salt thereof, wherein R$_1$ is H, phenyl, methyl, ethyl, propyl, trifluoromethyl or hydroxymethyl.

6. The benzopyrone derivative according to claim 1 or the pharmaceutically acceptable salt thereof, wherein R$_3$, R$_4$ and R$_5$ are each independently H, halogen or C$_{1-5}$alkyl.

7. The benzopyrone derivative according to claim 6 or the pharmaceutically acceptable salt thereof, wherein R$_3$ is H, Cl or methyl; R$_4$ is H, Cl or methyl; and R$_5$ is H, F or methyl.

8. The benzopyrone derivative according to claim 1 or the pharmaceutically acceptable salt thereof, wherein R$_2$ is H or methyl.

9. The benzopyrone derivative according to claim 1 or the pharmaceutically acceptable salt thereof, wherein when Q is CH, X is O, and R$_5$ is F; when Q is N, X is S, and R$_5$ is H.

10. The benzopyrone derivative according to claim 1 or the pharmaceutically acceptable salt thereof, which is selected from the group consisting of:

7-(4-(4-(3-(6-fluoro-benzisoxazole)-1-piperidyl)-n-butoxy))-2H-benzopyran-2-one;

7-(4-(4-(3-(1,2-benzisothiazole)-1-piperazinyl)-n-butoxy))-2H-benzopyran-2-one;

7-(3-(4-(3-(6-fluoro-benzisoxazole)-1-piperidyl)-n-propoxy))-2H-benzopyran-2-one;

7-(3-(4-(3-(1,2-benzisothiazole)-1-piperazinyl)-n-propoxy))-2H-benzopyran-2-one;

7-(4-(4-(3-(1,2-benzisothiazole)-1-piperazinyl)-n-butoxy))-4-methyl-2H-benzopyran-2-one;

7-(4-(4-(3-(6-fluoro-benzisoxazole)-1-piperidyl)-n-butoxy))-4-methyl-2H-benzopyran-2-one;

7-(3-(4-(3-(6-fluoro-benzisoxazole)-1-piperidyl)-n-propoxy))-4-methyl-2H-benzopyran-2-one;

7-(3-(4-(3-(1,2-benzisothiazole)-1-piperazinyl)-n-propoxy))-4-methyl-2H-benzopyran-2-one;
7-(5-(4-(3-(6-fluoro-benzisoxazole)-1-piperidyl)-n-pentyloxy))-4-methyl-2H-benzopyran-2-one;
(E)-7-(4-(4-(3-(6-fluoro-benzisoxazole)-3-piperidyl)-but-2-enyloxy))-4-methyl-2H-benzopyran-2-one;
7-(3-(4-(3-(1,2-benzisothiazole)-1-piperazinyl)-n-propoxy))-4-phenyl-2H-benzopyran-2-one;
7-(4-(4-(3-(6-fluoro-benzisoxazole)-1-piperidyl)-n-butoxy))-4-phenyl-2H-benzopyran-2-one;
7-(4-(4-(3-(1,2-benzisothiazole)-1-piperazinyl)-n-butoxy))-4-phenyl-2H-benzopyran-2-one;
7-(3-(4-(3-(6-fluoro-benzisoxazole)-1-piperidyl)-n-propoxy))-4-(trifluoromethyl)-2H-benzopyran-2-one;
7-(3-(4-(3-(1,2-benzisothiazole)-1-piperazinyl)-n-propoxy))-4-(trifluoromethyl)-2H-benzopyran-2-one;
7-(4-(4-(3-(6-fluoro-benzisoxazole)-1-piperidyl)-n-butoxy))-4-(trifluoromethyl)-2H-benzopyran-2-one;
7-(4-(4-(3-(1,2-benzisothiazole)-1-piperazinyl)-n-butoxy))-4-(trifluoromethyl)-2H-benzopyran-2-one;
7-(4-(4-(3-(6-fluoro-benzisoxazole)-1-piperidyl)-n-butoxy))-4-methyl-8-chloro-2H-benzopyran-2-one;
7-(4-(4-(3-(1,2-benzisothiazole)-1-piperazinyl)-n-butoxy))-4-methyl-8-chloro-2H-benzopyran-2-one;
7-(3-(4-(3-(6-fluoro-benzisoxazole)-1-piperidyl)-n-propoxy))-4-methyl-8-chloro-2H-benzopyran-2-one;
7-(3-(4-(3-(1,2-benzisothiazole)-1-piperazinyl)-n-propoxy))-4-methyl-8-chloro-2H-benzopyran-2-one;
7-(4-(4-(3-(6-fluoro-benzisoxazole)-1-piperidyl)-n-butoxy))-4,8-dimethyl-2H-benzopyran-2-one;
7-(4-(4-(3-(1,2-benzisothiazole)-1-piperazinyl)-n-butoxy))-4,8-dimethyl-2H-benzopyran-2-one;
7-(4-(4-(3-(6-fluoro-benzisoxazole)-1-piperidyl)-n-butoxy))-4-n-propyl-2H-benzopyran-2-one;
7-(4-(4-(3-(1,2-benzisothiazole)-1-piperazinyl)-n-butoxy))-4-n-propyl-2H-benzopyran-2-one;
7-(4-(4-(3-(6-fluoro-benzisoxazole)-1-piperidyl)-n-butoxy))-4-ethyl-2H-benzopyran-2-one;
7-(4-(4-(3-(1,2-benzisothiazole)-1-piperazinyl)-n-butoxy))-4-ethyl-2H-benzopyran-2-one;
7-(3-(4-(3-(6-fluoro-benzisoxazole)-1-piperidyl)-n-propoxy))-3,4-dimethyl-2H-benzopyran-2-one;
7-(4-(4-(3-(6-fluoro-benzisoxazole)-1-piperidyl)-n-butoxy))-3,4-dimethyl-2H-benzopyran-2-one;
7-(3-(4-(3-(6-fluoro-benzisoxazole)-1-piperidyl)-n-propoxy))-4-hydroxymethyl-2H-benzopyran-2-one;
7-(4-(4-(3-(6-fluoro-benzisoxazole)-1-piperidyl)-n-butoxy))-4-hydroxymethyl-2H-benzopyran-2-one;
7-(3-(4-(3-(6-fluoro-benzisoxazole)-1-piperidyl)-2-hydroxylpropoxy))-4-methyl-2H-benzopyran-2-one;
7-(3-(4-(3-(6-fluoro-benzisoxazole)-1-piperidyl)-2-hydroxylpropoxy))-4-phenyl-2H-benzopyran-2-one;
7-(4-(4-(3-(6-fluoro-benzisoxazole)-1-piperidyl)-n-propoxy))-4-phenyl-benzopyran-2-one;
and their pharmaceutically acceptable salts.

11. The benzopyrone derivative according to claim 1 or the pharmaceutically acceptable salt thereof, wherein the pharmaceutically acceptable salt of the compound having the structure of formula (I) is selected from the group consisting of hydrochloride, hydrobromide, hydriodate, nitrate, sulfate or bisulfate, phosphate or acid phosphate, acetate, lactate, citrate, tartrate, maleate, fumarate, mesylate, gluconate, saccharate, benzoate, ethanesulfonate, benzenesulfonate, p-toluenesulfonate.

12. A pharmaceutical composition, comprising the benzopyrone derivative according to claim 1 or the pharmaceutically acceptable salt thereof, and pharmaceutically acceptable adjuvant.

13. A method for treating schizophrenia, comprising administrating benzopyrone derivative according to claim 1 or the pharmaceutically acceptable salt thereof to a patient in need thereof.

* * * * *